US009085597B2

(12) United States Patent
Konishi et al.

(10) Patent No.: US 9,085,597 B2
(45) Date of Patent: Jul. 21, 2015

(54) METHOD FOR PRODUCING DIESTER OF POLYHYDRIC ALCOHOL AND FATTY ACID (75) Inventors: Kazunobu Konishi, Tokyo (JP); Mayumi Sato, Tokyo (JP); Makoto Okamoto, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 44 days.

(21) Appl. No.: 14/006,313

(22) PCT Filed: Mar. 21, 2012

(86) PCT No.: PCT/JP2012/057194
§ 371 (c)(1),
(2), (4) Date: Nov. 15, 2013

(87) PCT Pub. No.: WO2012/137604
PCT Pub. Date: Oct. 11, 2012

(65) Prior Publication Data
US 2014/0142295 A1    May 22, 2014

(30) Foreign Application Priority Data

Apr. 1, 2011 (JP) ................................. 2011-081902
Nov. 15, 2011 (JP) ................................. 2011-249569

(51) Int. Cl.
*C07H 7/02* (2006.01)
*C07H 13/06* (2006.01)
*C07C 67/03* (2006.01)
*C07H 1/00* (2006.01)

(52) U.S. Cl.
CPC ....... *C07H 7/02* (2013.01); *C07C 67/03* (2013.01); *C07H 1/00* (2013.01); *C07H 13/06* (2013.01); *C07C 2101/14* (2013.01)

(58) Field of Classification Search
None
See application file for complete search history.

(56) References Cited

FOREIGN PATENT DOCUMENTS

| CN | 1656111 A | 8/2005 |
| EP | 0254376 A1 | 1/1988 |
| JP | 63-119493 A | 5/1988 |
| JP | 02-295995 A | 12/1990 |
| JP | 2002-241328 A | 8/2002 |
| JP | 2004-269429 A | 9/2004 |
| JP | 2005-314592 A | 11/2005 |
| WO | 03/099838 A1 | 12/2003 |

OTHER PUBLICATIONS

International Search Report issued in corresponding International Patent Application No. PCT/JP2012/057194 dated Jun. 12, 2012.
Therisod et al., "Regioselective Acylation of Secondary Hydroxyl Groups in Sugars Catalyzed by Lipases in Organic Solvents," Journal of American Chemical Society, 109: 3977-3981 (1987).
Zhang et al., "Efficient lipase-selective synthesis of dilauryl mannoses by simultaneous reaction-extraction system," Biotechnology Letters, 31: 423-428 (2009).
Xie et al., "Calcined Mg-Al hydrotalcites as solid base catalysts for methanolysis of soybean oil," Journal of Molecular Catalysis A: Chemical, 246: 24-32 (2006).
Office Action issued in counterpart Taiwanese Patent Application No. 101111021 dated Oct. 9, 2013.
Corma et al., "Lewis and Brönsted basic active sites on solid catalysts and their role in the synthesis of monoglycerides," Journal of Catalysis, 234: 340-347 (2005).
International Preliminary Report on Patentability issued in counterpart International Patent Application No. PCT/JP2012/057194 dated Oct. 17, 2013.
Corma et al., "Catalysts for the Production of Fine Chemicals: Production of Food Emulsifiers, Monoglycerides, by Glycerolysis of Fats with Solid Base Catalysts," Journal of Catalysts, 173: 315-321 (1998).
Extended European Search Report issued in counterpart European Patent Application No. 12768286.2 dated Mar. 6, 2014.
Barakos et al., "Transesterification of triglycerides in high and low quality oil feeds over an HT2 hydrotalcite catalyst," Bioresource Technology, 99: 5037-5042 (2008).

*Primary Examiner* — Layla Bland
(74) *Attorney, Agent, or Firm* — Morgan, Lewis & Bockius LLP (57) ABSTRACT

A method for producing a diester of polyhydric alcohol and fatty acid, comprising a step of reacting a monoester of polyhydric alcohol and fatty acid in the presence of a catalyst containing a hydrotalcite compound to obtain a diester of polyhydric alcohol and fatty acid.

18 Claims, 2 Drawing Sheets

METHOD FOR PRODUCING DIESTER OF POLYHYDRIC ALCOHOL AND FATTY ACID

TECHNICAL FIELD

The present invention relates to a method for producing a diester of polyhydric alcohol and fatty acid.

BACKGROUND ART

Esters of sugar alcohol and fatty acid, which are condensates of polyhydric alcohol and fatty acid, are widely used as nonionic surfactants added to foods, cosmetics, pharmaceuticals, detergents for kitchen, and the like because an ester of sugar alcohol and fatty acid has a remarkable interface activity, good biodegradability and safety, and the like.

As an industrial production method for an ester of polyhydric alcohol and fatty acid, a method for heating a polyhydric alcohol and a fatty acid in the presence of a catalyst (or in the absence of a catalyst), and the like are known.

Moreover, Patent Literature 1 describes a method for producing an ester of sugar alcohol and fatty acid, wherein a sugar alcohol having 4 to 6 carbon atoms and a lower alcohol ester of a fatty acid are subjected to a transesterification reaction in the presence of an alkali metal salt.

Moreover, Non Patent Literatures 1 and 2 describe methods for producing an ester of sugar and fatty acid using an enzyme.

CITATION LIST

Patent Literature

Patent Literature 1: Japanese Patent Application Laid-Open No. 2004-269429
Patent Literature 2: Japanese Patent Application Laid-Open No. 2-295995

Non Patent Literature

Non Patent Literature 1: J. Am. Chem. Soc., Vol. 109 (13), pp. 3977-3981 (1987)
Non Patent Literature 2: Biotechnol. Lett., Vol. 31, pp. 423-428 (2009)

SUMMARY OF INVENTION

Technical Problem

Esters of polyhydric alcohol and fatty acid include monoesters, diesters, triesters, and the like. Among these, diesters are difficult to selectively obtain.

For example, in the industrial production method, an ester of polyhydric alcohol and fatty acid is obtained by dehydration condensation of a polyhydric alcohol and a fatty acid, but the selectivity of the diester is remarkably low, and a complex refining operation (see Patent Literature 2, for example) is necessary to obtain a diester with high precision.

Moreover, even in the method described in Patent Literature 1, if an attempt is made to obtain esters of sugar alcohol and fatty acid with a high ratio of diesters, generation of triesters is not avoided, and the diesters are difficult to selectively synthesize.

Moreover, although high selectivity may be obtained in the methods using an enzyme described in Non Patent Literatures 1 and 2, these methods have defects such that the reaction rate is low, an enzyme as a catalyst is expensive but cannot escape degradation if the enzyme is repeatedly used for the reaction.

An object of the present invention is to provide a method for producing a diester of polyhydric alcohol and fatty acid, by which a diester of polyhydric alcohol and fatty acid can be obtained efficiently.

Solution to Problem

The present inventors conducted extensive research in order to attain the above object, and found out that surprisingly, by using a hydrotalcite compound as a catalyst, a disproportionation reaction progresses to generate, from two molecules of a monoester of polyhydric alcohol and fatty acid, one molecule of a diester of polyhydric alcohol and fatty acid and one molecule of the polyhydric alcohol. Thus, the present invention has been completed.

The present invention has aspects described below.

[1] A method for producing a diester of polyhydric alcohol and fatty acid, comprising a step of reacting a monoester of polyhydric alcohol and fatty acid in the presence of a catalyst containing a hydrotalcite compound to obtain a diester of polyhydric alcohol and fatty acid.
[2] The method according to [1], wherein the polyhydric alcohol constituting the monoester of polyhydric alcohol and fatty acid is a sugar or a sugar alcohol.
[3] The method according to [1] or [2], wherein the hydrotalcite compound is a compound represented by the following formula (1):

$$(M^{2+})_{1-x}(M^{3+})_x(OH^-)_{2+x-y}(A^{n-})_{y/n} \quad (1)$$

[wherein $M^{2+}$ represents a divalent metal ion, $M^{3+}$ represents a trivalent metal ion, $A^{n-}$ represents an n-valent anion, x represents a positive number of 0.1 to 0.5, y represents a positive number of 0.1 to 0.5, and n represents an integer of 1 or 2].
[4] The method according to any one of [1] to [3], wherein the fatty acid constituting the monoester of polyhydric alcohol and fatty acid has 4 to 24 carbon atoms.
[5] The method according to any one of [1] to [4], wherein the polyhydric alcohol constituting the monoester of polyhydric alcohol and fatty acid is a monosaccharide.
[6] The method according to [5], wherein the monosaccharide includes at least one selected from the group consisting of glucose, fructose, and galactose.
[7] The method according to any one of [1] to [4], wherein the polyhydric alcohol constituting the monoester of polyhydric alcohol and fatty acid is inositol.
[8] The method according to [7], wherein the inositol is myo-inositol.
[9] The method according to any one of [1] to [8], wherein the step is performed in a reaction solution containing at least one solvent selected from the group consisting of an ether compound, a ketone compound, a nitrile compound, a halogenated alkyl compound, a tertiary alcohol compound, an amide compound, an amine compound, a sulfoxide compound, and a linear hydrocarbon compound having 5 to 8 carbon atoms.
[10] The method according to any one of [1] to [9], wherein a reaction temperature in the step is 50 to 100° C.

Advantageous Effects of Invention

According to the present invention, a method for producing a diester of polyhydric alcohol and fatty acid, by which a diester of polyhydric alcohol and fatty acid can be obtained efficiently is provided.

DESCRIPTION OF EMBODIMENTS

Suitable embodiments of the diester of polyhydric alcohol and fatty acid according to the present invention will be described below.

The method for producing a diester of polyhydric alcohol and fatty acid according to the present embodiment includes a step of reacting a monoester of polyhydric alcohol and fatty acid in the presence of a catalyst containing a hydrotalcite compound to obtain a diester of polyhydric alcohol and fatty acid.

In the production method according to the present embodiment, by using a catalyst containing a hydrotalcite compound, the disproportionation reaction progresses to generate, from two molecules of a monoester of polyhydric alcohol and fatty acid, one molecule of a diester of polyhydric alcohol and fatty acid and one molecule of the polyhydric alcohol. Here, the hydrotalcite compound is a crystalline layered composite metal hydroxide having a layer composed of a metal ion and a layer composed of an anion and/or a water molecule.

If such a disproportionation reaction is performed using a base catalyst, for example, the generated diester of polyhydric alcohol and fatty acid further reacts, and successively a triester of polyhydric alcohol and fatty acid, a tetraester of polyhydric alcohol and fatty acid, and the like generate. For this reason, in such a method, it is difficult to obtain a diester of polyhydric alcohol and fatty acid with good selectivity.

In contrast, in the disproportionation reaction in the production method according to the present embodiment, because the specific catalyst is used, the successive reaction to generate the triester of polyhydric alcohol and fatty acid, tetraester of polyhydric alcohol and fatty acid, and the like hardly occurs. For this reason, according to the production method according to the present embodiment, the diester of polyhydric alcohol and fatty acid can be obtained with very high selectivity.

As the hydrotalcite compound, know or commercially available compounds can be used. Compounds produced by known production methods can be used. The hydrotalcite compound may be a natural hydrotalcite compound or may be a synthetic hydrotalcite compound, and it is preferable to use synthetic hydrotalcite compounds.

In the production method according to the present embodiment, particularly, the hydrotalcite compound represented by the following formula (1) can be suitably used:

$$(M^{2+})_{1-x}(M^{3+})_x(OH^-)_{2+x-y}(A^{n-})_{y/n} \quad (1)$$

wherein $M^{2+}$ represents a divalent metal ion, $M^{3+}$ represents a trivalent metal ion, $A^{n-}$ represents an n-valent anion, x represents a positive number of 0.1 to 0.5, y represents a positive number of 0.1 to 0.5, and n represents an integer of 1 or 2.

As the divalent metal ion, for example, at least one selected from the group consisting of $Mg^{2+}$, $Ca^{2+}$, $Fe^{2+}$, $Zn^{2+}$, and $Cu^{2+}$ can be used. Among these, $Mg^{2+}$ and $Ca^{2+}$ are preferable as the divalent metal ion. $M^{2+}$ may be composed of one metal ion, or may be composed of two or more metal ions.

As the trivalent metal ion, for example, at least one selected from the group consisting of $Al^{3+}$ and $Fe^{3+}$ can be used. $M^{3+}$ may be composed of one metal ion, or may be composed of two or more metal ions.

It is preferred that the molar ratio ($M^{2+}/M^{3+}$) of the divalent metal ion to the trivalent metal ion in the hydrotalcite compound be 2 to 7, more preferred that the molar ratio be 2 to 5, and still more preferred that the molar ratio be 2 to 4. According to a catalyst containing such a hydrotalcite compound, higher catalyst activity is obtained. The molar ratio ($M^{2+}/M^{3+}$) can also be expressed as (1−x)/x.

Examples of the anion include $CO_3^{2-}$, $Cl^-$, $OH^-$, $NO_2^-$, $NO_3^-$, and $SO_4^{2-}$. Among these, it is preferable that the anion contain at least one of $CO_3^{2-}$ and $Cl^-$.

The hydrotalcite compound used in the production method according to the present embodiment may be an anhydride, or may be a hydrate.

Examples of the hydrotalcite compound include compounds represented by formulas such as $Mg_4Al_2(OH)_{12}Cl_2$, $Mg_4Al_2(OH)_{12}CO_3$, $Mg_6Al_2(OH)_{16}Cl_2$, $Mg_6Al_2(OH)_{16}CO_3$, $Mg_{10}Al_2(OH)_{24}Cl_2$, $Mg_{10}Al_2(OH)_{24}CO_3$, $Ca_3Al_2(OH)_{10}Cl_2$, $Ca_3Al_2(OH)_{10}CO_3$, $Ca_4Al_2(OH)_{10}Cl_2$, $Ca_4Al_2(OH)_{10}CO_3$, $Ca_4Mg_6Al_5(OH)_{10}Cl_2$, and $Ca_4Mg_6Al_5(OH)_{10}CO_3$, and hydrates thereof (such as $Mg_6Al_2(OH)_{16}CO_3 \cdot 4H_2O$).

As the hydrotalcite compound, for example, a hydrotalcite compound containing 34 to 38% by mass of $Mg^{2+}$ in terms of magnesium oxide and 13 to 19% by mass of $Al^{3+}$ in terms of aluminum oxide can be suitably used.

It is preferable that the liquid pH of the hydrotalcite compound be 8 to 10. It is preferable that the loss on drying of the hydrotalcite compound be 10% or less. Examples of the hydrotalcite compound having the physical properties include commercially available products "Tomita-AD 500NS" (made by Tomita Pharmaceutical Co., Ltd.). This commercially available product contains 37% by weight of $Mg^{2+}$ in terms of magnesium oxide and 16% by weight of $Al^{3+}$ in terms of aluminum oxide, and has physical properties of the liquid pH of approximately 8.9 and the loss on drying of 5.7%.

The method for producing a hydrotalcite compound is not particularly limited, and the hydrotalcite compound can be produced by the following method, for example. First, a solution containing the divalent metal ion and the trivalent metal ion (first solution) is prepared, and a solution containing the anion and an alkali (second solution) is prepared. Then, a precipitate deposited by mixing the two solutions is dried. Thus, a hydrotalcite compound can be obtained.

More specifically, for example, when the divalent metal ion is $Mg^{2+}$, the trivalent metal ion is $Al^{3+}$, the anion is $CO_3^{2-}$, a water-soluble magnesium salt and a water-soluble aluminum salt are dissolved in water to prepare the first solution, a carbonate salt and sodium hydroxide are dissolved in water to prepare the second solution. The two solutions are mixed, and stirred at 60° C. to 70° C. for 12 to 24 hours, and a deposited precipitate is recovered. Next, the recovered precipitate is washed with water when necessary, and dried at approximately 100° C. to 120° C. to obtain a hydrotalcite compound.

The monoester of polyhydric alcohol and fatty acid is a condensate of one molecule of a polyhydric alcohol and one molecule of a fatty acid, and the diester of polyhydric alcohol and fatty acid is a condensate of one molecule of a polyhydric alcohol and two molecules of a fatty acid.

Examples of the fatty acid constituting the monoester of polyhydric alcohol and fatty acid include saturated fatty acids with a linear structure and unsaturated fatty acids with a linear structure. The fatty acid may be a fatty acid of a dicarboxylic acid type. The fatty acid has preferably 4 to 24 carbon atoms, and may have 6 to 20 carbon atoms or 6 to 16 carbon atoms.

The polyhydric alcohol constituting the monoester of polyhydric alcohol and fatty acid is a compound having two or more hydroxyl groups. The number of hydroxyl groups that the polyhydric alcohol has is preferably 3 or more, more preferably 4 or more, and may be 12 or less or 10 or less.

Examples of the polyhydric alcohol include sugar, sugar alcohol, ethylene glycol, propanediol, butanediol, butanetriol, cyclobutanediol, butanetetraol, cyclobutanetetraol, pentanediol, cyclopentanediol, pentanetriol, pentanetetraol, cyclopentanetriol, hydroquinone, catechol, and benzenetriol.

The monoester of polyhydric alcohol and fatty acid may be prepared by any method. For example, the monoester of polyhydric alcohol and fatty acid can be prepared by: 1) a method for directly performing esterification using a fatty acid chloride or an anhydrous fatty acid and a polyhydric alcohol as raw materials, 2) a method for performing ester exchange using a fatty acid ester and a polyhydric alcohol as raw materials in which the fatty acid ester is a condensate of an alcohol having a small number of carbon atoms and a fatty acid, 3) a method using an enzyme such as lipase as a catalyst, and 4) a fermentation method using a microorganism.

As the raw material used in the disproportionation reaction, the monoester of polyhydric alcohol and fatty acid can be used alone, or a mixture of the monoester of polyhydric alcohol and fatty acid and the diester of polyhydric alcohol and fatty acid can be used. Moreover, a mixture further containing a triester of polyhydric alcohol and fatty acid, a tetraester of polyhydric alcohol and fatty acid, and the like as the raw material can be used.

Namely, for example, when the mixture of the monoester of polyhydric alcohol and fatty acid and the diester of polyhydric alcohol and fatty acid is obtained as the reaction product by the condensation reaction of the polyhydric alcohol with the fatty acid, the monoester of polyhydric alcohol and fatty acid can be isolated from the mixture and fed to the disproportionation reaction. Moreover, the mixture can be fed as it is to the disproportionation reaction.

In the disproportionation reaction in the production method according to the present embodiment, because the specific catalyst is used, the successive reaction from the diester of polyhydric alcohol and fatty acid to the triester of polyhydric alcohol and fatty acid and the tetraester of polyhydric alcohol and fatty acid hardly occurs. For this reason, even if the diester of polyhydric alcohol and fatty acid is mixed in the raw material, a by-product such as the triester of polyhydric alcohol and fatty acid is hardly produced, and the diester of polyhydric alcohol and fatty acid can be obtained with high selectivity.

The disproportionation reaction can be performed, for example, by keeping a reaction solution at a predetermined reaction temperature, the reaction solution being obtained by dissolving and/or dispersing the catalyst and the monoester of polyhydric alcohol and fatty acid in a reaction solvent.

The amount of the monoester of polyhydric alcohol and fatty acid in the reaction solution is not particularly limited, and can be properly adjusted according to the saturated solubility in the reaction solvent, for example. For example, by dissolving the monoester of polyhydric alcohol and fatty acid in the reaction solution near to the saturated solubility thereof, reactivity and productivity can be further improved.

The monoester of polyhydric alcohol and fatty acid may not always be dissolved in the reaction solution. For example, the monoester of polyhydric alcohol and fatty acid may be fed into the reaction solution beyond the saturated solubility. In this case, the reaction is the reaction in the so-called slurry state, in which a solid monoester of polyhydric alcohol and fatty acid exists in the initial period of the reaction. Even in such a case, the disproportionation reaction progresses. As the disproportionation reaction progresses, the monoester of polyhydric alcohol and fatty acid gradually dissolves, and is converted into the diester of polyhydric alcohol and fatty acid until the equilibrium point is finally reached.

The reaction solvent may be solvents that do not inhibit the disproportionation reaction (transesterification reaction), and various organic solvents, ionic liquids, and supercritical fluids can be used. Examples of the organic solvents include ether compounds such as dimethyl ether, diethyl ether, methyl ethyl ether, 1,2-dimethoxyethane, and ethylene glycol dimethyl ether; ketone compounds such as acetone, methyl ethyl ketone, diethyl ketone, dipropyl ketone, dibutyl ketone, methyl isobutyl ketone, and 2,4-pentanedione; nitrile compounds such as acetonitrile, acrylonitrile, propionitrile, adiponitrile, and isobutyronitrile; halogenated alkyl compounds such as chloroform, methylene chloride, carbon tetrachloride, and 1,2-dichloroethane; tertiary alcohol compounds such as tert-butyl alcohol; amide compounds such as dimethylformamide and dimethylacetoamide; amine compounds such as ethylenediamine and hexamethylenediamine; and sulfoxide compounds such as dimethyl sulfoxide. Examples of the ionic liquids include imidazolium compounds, pyridinium compounds, quaternary ammonium compounds, and phosphonium compounds, and specifically include 1-butyl-3-methylimidazolium hexafluorophosphate and 1-butyl-3-methylimidazolium tetrafluoroborate. Examples of the supercritical fluids include supercritical carbon dioxide.

It is preferable that the reaction solvent from which the water content is removed as much as possible by performing a dehydration treatment or the like be used. A very small amount of water causes no problem, but if the content of water is larger, a hydrolysis reaction in addition to the disproportionation reaction (transesterification reaction) competes. As a result, a fatty acid is easily produced as a by-product. If the fatty acid is produced as a by-product, separation and refining of the diester of polyhydric alcohol and fatty acid may be difficult.

For the reaction temperature, 35 to 100° C. is preferred, 50 to 90° C. is more preferred, and 50 to 75° C. is still more preferred. If the reaction temperature is within this range, reactivity and productivity are remarkably improved. If the reaction temperature is excessively low, reactivity and productivity tend to be difficult to improve. If the reaction temperature is excessively high, reactivity and productivity may reduce. The cause for reactivity and productivity to reduce by increasing the reaction temperature is not clear, but it is thought that degradation of the catalyst due to a high temperature occurs, or catalyst activity is inhibited.

The reaction pressure in the disproportionation reaction is not particularly limited, and may be atmospheric pressure. The composition of the gaseous phase portion in the disproportionation reaction is not particularly limited. Usually, an inert gas such as nitrogen is selected from the viewpoints of safety such as prevention of explosion and suppression of the oxidation reaction.

The disproportionation reaction can be performed until the reaction reaches the equilibrium point at which apparent generation of the diester of polyhydric alcohol and fatty acid stops. The time to reach the equilibrium point varies according to the composition of the raw material to be used, the concentration of the raw material, the reaction temperature, the concentration of the catalyst, the kind of the reaction solvent, and the like. The reaction time can be 1 to 72 hours, for example.

The amount of the catalyst to be used in the disproportionation reaction can be properly adjusted according to the composition of the raw material to be used, the concentration of the raw material, the reaction temperature, the kind of the organic solvent, and the like. If the amount is excessively small, it is disadvantageous from the viewpoint of productivity. If the amount is excessively large, problems may arise in stirring or the like. Accordingly, it is preferable that the amount of the catalyst to be used based on 1 L of the reaction solvent be 1 to 500 g/L.

In the reaction solution after completion of the reaction in the disproportionation reaction, the catalyst, the diester of polyhydric alcohol and fatty acid, the polyhydric alcohol, and the unreacted monoester of polyhydric alcohol and fatty acid (or monoester of polyhydric alcohol and fatty acid generated at the equilibrium reaction) in some cases are contained. In the case where a low polar solvent is used as the reaction solvent, the diester of polyhydric alcohol and fatty acid (or a mixture of the diester of polyhydric alcohol and fatty acid and the monoester of polyhydric alcohol and fatty acid) can be obtained, for example, by separating a solid catalyst and polyhydric alcohol from the reaction solution by a standard solid liquid separation method, and distilling the reaction solvent away.

In the case where a polar solvent is used as the reaction solvent, the diester of polyhydric alcohol and fatty acid (or a mixture of the diester of polyhydric alcohol and fatty acid and the monoester of polyhydric alcohol and fatty acid) can be obtained, for example, by adding the low polar solvent to the reaction solution to deposit polyhydric alcohol, separating a solid catalyst and the deposited polyhydric alcohol from the reaction solution by a standard solid liquid separation method, and distilling the reaction solvent and the added low polar solvent away.

The catalyst recovered from the reaction solution can be reused as it is for the disproportionation reaction. In the case where the catalyst is repeatedly used for the disproportionation reaction and degraded, the catalyst can be activated by removing impurities such as a coloring substance adhering to the catalyst by a standard solvent washing, an oxidation treatment, a burning treatment, or the like.

The reaction solution after the catalyst and polyhydric alcohol are separated therefrom is usually colorless and transparent. In the case where coloring occurs, decolorization is performed on the catalyst by a standard bleaching treatment using a hydrogen peroxide solution or hypochlorous acid; a decolorizing treatment using an adsorbent such as activated carbon, ion exchange resin, and active alumina; or the like, and distilling the reaction solvent and the like away.

The reaction mode of the disproportionation reaction is not particularly limited, and a batch reaction mode using a standard stirring tank; a semi-batch reaction mode while necessary raw materials are added; a continuous reaction mode in which the catalyst is molded into a shape having a constant particle size or more, fixing the catalyst inside of a stirring tank or a tubular reactor, and performing addition of the necessary raw materials and extraction of the reaction product at the same time; and the like can be used.

The reaction conversion rate of the monoester of polyhydric alcohol and fatty acid in the disproportionation reaction can be properly adjusted according to the reaction temperature, the reaction time, the amount of the catalyst to be used, and the like. A preferable reaction conversion rate depends on the composition of the raw material, physical properties such as the interface activity demanded of the target product, and the like, but usually, it is preferable that conversion be performed at an extent in which the interface activity of the raw material is compared with that of the product and can be distinguished therefrom. It is needless to say that the reaction conversion rate is limited to the equilibrium conversion rate or less that is determined by the raw material composition, the reaction condition, and the like. It is preferred that the reaction conversion rate of the monoester of polyhydric alcohol and fatty acid be 10% or more, it is more preferred that the reaction conversion rate of the monoester of polyhydric alcohol and fatty acid be 15% or more, and it is still more preferred that the reaction conversion rate of the monoester of polyhydric alcohol and fatty acid be 20% or more.

Hereinafter, the production method according to the present embodiment will be described using examples of an aspect when the polyhydric alcohol is a sugar and an aspect when the polyhydric alcohol is a sugar alcohol.

(About Ester of Sugar and Fatty Acid)

Esters of sugar and fatty acid, which are condensates of sugar and fatty acid, are widely used as nonionic surfactants added to foods, cosmetics, pharmaceuticals, detergents for kitchen, and the like because an ester of sugar and fatty acid has a remarkable interface activity, good biodegradability and safety, and the like.

Examples of a method for producing an ester of sugar and fatty acid include 1) a method for directly performing esterification using a fatty acid chloride or an anhydrous fatty acid and a sugar as raw materials, 2) a method for performing ester exchange using a fatty acid ester and a sugar as raw materials in which the fatty acid ester is a condensate of an alcohol having a small number of carbon atoms and a fatty acid, 3) a method using an enzyme such as lipase as a catalyst, and 4) a fermentation method using a microorganism.

Among these, the method 1) is used for synthesis on a laboratory scale, but the raw materials are expensive, not economical, and not commercialized until now.

The method 3) is a promising method because the position selectivity of the sugar in the esterification reaction is high. For example, the above Non Patent Literature 1 discloses a method as the method for synthesizing an ester of sugar and fatty acid selectively by an enzyme method using lipase in which using lipase derived from *Chromobactrrium viscosum* and n-Octyl-β-Glucopyranoside and 6-O-butylglucose as raw materials, a monoester (C-6 position) and a diester (C-3,6 position) are synthesized at 1:1.

Moreover, the above Non Patent Literature 2 discloses a method in which using *Candida* Antarctica lipase B (Novozyme SP435) immobilized lipase, and a mixture of diesters (C-1,6 position, C-3,6 position, and C-4,6 position) is synthesized with lauric acid and mannose as raw materials at a yield of 51%.

However, the method 3) has defects such that the reaction rate is slow, and an enzyme, such as lipase, used as a catalyst is expensive but cannot escape degradation if the enzyme is repeatedly used for the reaction. For these reasons, large-scale commercialization is not attained.

Further, synthesis of an ester of sugar and fatty acid by the method 4) has been commercialized recently. However, in the synthesis of an ester of sugar and fatty acid by the method 4), a load of separation and refining of a product from an aqueous fermentation solution is large, cost is high, and the application for use is limited.

For this reason, at present, the sucrose fatty acid ester representative of esters of sugar and fatty acid industrially mass-produced is produced by the method 2), and specifically by a method for performing ester exchange in the presence of a base catalyst using sucrose and a fatty acid methyl ester as raw materials and dimethyl formamide (DMF) or dimethyl sulfoxide (DMSO) as a solvent.

However, the composition of the ester of sugar and fatty acid obtained by this method is a mixture of monoesters, diesters, triesters, and the like, and generation of triesters cannot be avoided particularly when an attempt is made to obtain an ester of sugar and fatty acid with a high ratio of the diester. For this reason, a refining operation is necessary to obtain an ester of sugar and fatty acid with a high ratio of diesters by the above method.

In this respect, the above Patent Literature 1 discloses a method for separating and refining a mixture of esters of sugar and fatty acid obtained by transesterification reaction with a base catalyst, for example, a method for separating highly hydrophilic sucrose fatty acid esters from highly lipophilic sucrose fatty acid esters by changing an aqueous solution prepared at a predetermined sucrose fatty acid ester concentration to an acidic side.

However, in the method described in Patent Literature 1, when highly lipophilic sucrose fatty acid esters are obtained, they are obtained in a state where mainly diesters and triesters are mixed. Moreover, by-production of hydrophilic sucrose fatty acid esters (mainly, monoesters) is not avoided. This method is not always an efficient production method. The interface activity of the monoester of sugar and fatty acid is lower than that of the diester of sugar and fatty acid. Meanwhile, no remarkable improvement in interface activity is found even if the diester of sugar and fatty acid is turned into the triester of sugar and fatty acid, and the output level of the fatty acid ester worsens, leading to increase in cost.

In contrast, according to the production method according to the present embodiment, the diester of sugar and fatty acid can be obtained efficiently in a practical reaction time.

Examples of the sugar constituting the monoester of sugar and fatty acid include monosaccharides such as polyhydroxy aldehyde (aldose) and polyhydroxy ketone (ketose); and oligosaccharides that can be converted into monosaccharides by hydrolysis such as disaccharides and trisaccharides.

Examples of monosaccharides include biose, triose, tetrose, pentose, hexose, and heptose. The monosaccharides may be a D form or an L form.

More specifically, examples of ketotriose include dihydroxy acetone, and examples of aldotriose include glyceraldehyde. Examples of ketotetrose include erythrulose, and examples of aldotetrose include erythrose and threose. Examples of ketopentose include ribulose and xylulose, and examples of aldopentose include ribose, arabinose, xylose, and lyxose.

Examples of ketohexose include psicose, fructose, sorbose, and tagatose, and examples of aldohexose include allose, altrose, glucose, mannose, gulose, idose, galactose, and talose. Further, examples of ketoheptose include sedoheptulose.

Examples of the disaccharides include sucrose, lactose, maltose, trehalose, turanose, and cellobiose.

Examples of trisaccharides include raffinose, melezitose, and maltotriose.

Among these, sucrose, lactose, maltose, D-glucose, D-fructose, and D-galactose are preferable as the sugar constituting the monoester of sugar and fatty acid.

As the sugar constituting the monoester of sugar and fatty acid, monosaccharides are preferable. Namely, it is preferable that the monoester of sugar and fatty acid be at least one selected from the group consisting of glucose monoesters, fructose monoesters, and galactose monoesters.

The monoester of sugar and fatty acid may be prepared by any method. For example, the monoester of sugar and fatty acid can be prepared by: 1) a method for directly performing esterification using a fatty acid chloride or an anhydrous fatty acid and a sugar as raw materials, 2) a method for performing ester exchange using a fatty acid ester and a sugar as raw materials in which the fatty acid ester is a condensate of an alcohol having a small number of carbon atoms and a fatty acid, 3) a method using an enzyme such as lipase as a catalyst, and 4) a fermentation method using a microorganism.

Among these, it is preferable from the viewpoint of economy that by 2) the method for performing ester exchange, the monoester of sugar and fatty acid be prepared. In the case where the monoester of sugar and fatty acid is prepared by the method 2), it is desirable that the unreacted fatty acid ester be not contained in the raw material used for the disproportionation reaction. If the unreacted fatty acid ester is mixed, an extremely large load may be caused to separate the unreacted fatty acid ester from the diester of sugar and fatty acid obtained in the disproportionation reaction and refine the unreacted fatty acid ester.

For the raw material used in the disproportionation reaction, the monoester of sugar and fatty acid can be used alone, or a mixture of the monoester of sugar and fatty acid and the diester of sugar and fatty acid can be used. Moreover, the mixture further containing the triester of sugar and fatty acid, the tetraester of sugar and fatty acid, and the like can also be used.

Namely, for example, when the monoester of sugar and fatty acid is prepared by the transesterification reaction with a base catalyst, the reaction product to be obtained may be a mixture of the monoester of sugar and fatty acid and the diester of sugar and fatty acid. In this case, the monoester of sugar and fatty acid may be isolated from the reaction product and fed to the disproportionation reaction, or the reaction product may be fed as it is to the disproportionation reaction.

Because the specific catalyst is used in the disproportionation reaction in the production method according to the present embodiment as described above, the successive reaction from the diester of sugar and fatty acid to the triester of sugar and fatty acid or tetraester of sugar and fatty acid hardly occurs. For this reason, even if the diester of sugar and fatty acid is mixed in the raw material, a by-product such as triester of sugar and fatty acid is hardly produced, and the diester of sugar and fatty acid can be obtained with high selectivity.

In the disproportionation reaction, the catalyst can be properly selected according to the kind of monoesters of sugar and fatty acid. For example, in the disproportionation reaction of glucose adipic acid monoester, among the hydrotalcite compounds represented by the formula (1), it is preferred that the compound in which $M^{2+}$ is $Ca^{2+}$ be used as the catalyst, and it is more preferred that the compound in which $M^{2+}$ is $Ca^{2+}$ and $M^{3+}$ is $Al^{3+}$ be used as the catalyst. According to such a catalyst, the reactivity and diester selectivity in the disproportionation reaction are further improved.

Combinations of typical monoesters of sugar and fatty acid and particularly suitable hydrotalcite compounds as the catalyst for the disproportionation reaction are shown in Table 1. $M^{2+}$ and $M^{3+}$ in Table 1 represent $M^{2+}$ and $M^{3+}$ in the formula (1), respectively.

TABLE 1

| Monoester of sugar and fatty acid | Hydrotalcite compound | |
|---|---|---|
| | $M^{2+}$ | $M^{3+}$ |
| Glucose adipic acid monoester | $Ca^{2+}$ | $Al^{3+}$ |
| Glucose caprylic acid monoester | $Ca^{2+}$ | $Al^{3+}$ |
| Glucose pelargonic acid monoester | $Ca^{2+}$ | $Al^{3+}$ |

TABLE 1-continued

| | Hydrotalcite compound | |
|---|---|---|
| Monoester of sugar and fatty acid | $M^{2+}$ | $M^{3+}$ |
| Glucose capric acid monoester | $Mg^{2+}$ | $Al^{3+}$ |
| Glucose lauric acid monoester | $Mg^{2+}$ | $Al^{3+}$ |
| | $Ca^{2+}$ | $Al^{3+}$ |
| | $Ca^{2+}, Mg^{2+}$ | $Al^{3+}$ |
| | $Fe^{2+}$ | $Al^{3+}$ |
| | $Zn^{2+}$ | $Al^{3+}$ |
| Glucose pentadecylic acid monoester | $Mg^{2+}$ | $Al^{3+}$ |
| Glucose palmitic acid monoester | $Mg^{2+}$ | $Al^{3+}$ |
| Glucose dodecanedioic acid monoester | $Mg^{2+}$ | $Al^{3+}$ |
| Fructose lauric acid monoester | $Mg^{2+}$ | $Al^{3+}$ |
| Galactose lauric acid monoester | $Mg^{2+}$ | $Al^{3+}$ |

The disproportionation reaction can be performed, for example, by keeping the reaction solution at a predetermined reaction temperature, the reaction solution being prepared by dissolving and/or dispersing the catalyst and monoester of sugar and fatty acid in the reaction solvent.

The amount of the monoester of sugar and fatty acid in the reaction solution is not particularly limited, and can be properly adjusted according to saturated solubility in the reaction solvent, for example. Reactivity and productivity can be further improved, for example, by dissolving the monoester of sugar and fatty acid in the reaction solution near to the saturated solubility.

The monoester of sugar and fatty acid may not be always dissolved in the reaction solution. For example, the monoester of sugar and fatty acid may be fed into the reaction solution beyond the saturated solubility. In this case, the reaction is the reaction in the so-called slurry state, in which a solid monoester of sugar and fatty acid exists in the initial period of the reaction. Even in such a case, the disproportionation reaction progresses. As the disproportionation reaction progresses, the monoester of sugar and fatty acid gradually dissolves, and is converted into the diester of sugar and fatty acid until the equilibrium point is finally reached.

The reaction solvent may be solvents that do not inhibit the disproportionation reaction (transesterification reaction), and various organic solvents can be used. Examples of the reaction solvent include ether compounds such as dimethyl ether, diethyl ether, methyl ethyl ether, 1,2-dimethoxyethane, and ethylene glycol dimethyl ether; ketone compounds such as acetone, methyl ethyl ketone, diethyl ketone, dipropyl ketone, dibutyl ketone, methyl isobutyl ketone, and 2,4-pentanedione; nitrile compounds such as acetonitrile, acrylonitrile, propionitrile, adiponitrile, and isobutyronitrile; halogenated alkyl compounds such as chloroform, methylene chloride, carbon tetrachloride, and 1,2-dichloroethane; tertiary alcohol compounds such as tert-butyl alcohol; amide compounds such as dimethylformamide and dimethylacetoamide; amine compounds such as ethylenediamine and hexamethylenediamine; and sulfoxide compounds such as dimethyl sulfoxide.

Linear hydrocarbon compounds having 5 to 8 carbon atoms can also be used as the reaction solvent. In the case where the linear hydrocarbon compound is used as the reaction solvent, the disproportionation reaction exhibits a specific behavior. Specifically, the reaction progresses without a problem if pentane, hexane, and heptane are used. However, if octane is used, reactivity reduces. If linear hydrocarbon compounds having 9 or more carbon atoms such as nonane and decane are used, reactivity tends to remarkably reduce.

Among the above ether compounds, reactivity tends to reduce if a polymer such as polyethylene glycol is used. Accordingly, as the reaction solvent, low molecular linear ether compounds are preferable among the ether compounds.

Moreover, reactivity tends to reduce if a compound having a cyclic structure (for example, lactone compounds such as γ-butyrolactone, cyclic ether compounds such as tetrahydrofuran, and cyclic hydrocarbon compounds such as cyclohexane) is used. Accordingly, it is preferable that compounds having no cyclic structure be used as the reaction solvent. Namely, for example, as the reaction solvent, it is preferable that an alkyl group that the reaction solvent has be linear or branched. Besides, ionic liquids and supercritical fluids may be used as the reaction solvent. Examples of the ionic liquids include imidazolium compounds, pyridinium compounds, quaternary ammonium compounds, and phosphonium compounds, and specifically include 1-butyl-3-methylimidazolium hexafluorophosphate and 1-butyl-3-methylimidazolium tetrafluoroborate. Examples of the supercritical fluids include supercritical carbon dioxide.

It is preferable that the reaction solvent from which the water content is removed as much as possible by performing a dehydration treatment or the like be used. A very small amount of water causes no problem, but if the content of water is larger, a hydrolysis reaction in addition to the disproportionation reaction (transesterification reaction) competes. As a result, a fatty acid is easily produced as a by-product. If the fatty acid is produced as a by-product, separation and refining of the diester of sugar and fatty acid may be difficult.

For the reaction temperature, 35 to 100° C. is preferred, 50 to 90° C. is more preferred, and 50 to 75° C. is still more preferred. If the reaction temperature is within this range, reactivity and productivity are remarkably improved. If the reaction temperature is excessively low, reactivity and productivity tend to be difficult to improve. If the reaction temperature is excessively high, reactivity and productivity may reduce. The cause for reactivity and productivity to reduce by increasing the reaction temperature is not clear, but it is thought that degradation of the catalyst due to a high temperature occurs, or catalyst activity is inhibited.

The reaction pressure in the disproportionation reaction is not particularly limited, and may be atmospheric pressure. The composition of the gaseous phase portion in the disproportionation reaction is not particularly limited. Usually, an inert gas such as nitrogen is selected from the viewpoints of safety such as prevention of explosion and suppression of the oxidation reaction.

The disproportionation reaction can be performed until the reaction reaches the equilibrium point at which apparent generation of the diester of sugar and fatty acid stops. The time to reach the equilibrium point varies according to the composition of the raw material to be used, the concentration of the raw material, the reaction temperature, the concentration of the catalyst, the kind of the reaction solvent, and the like. The reaction time is usually 1 to 72 hours, preferably 2 to 20 hours, and more preferably approximately 3 to 5 hours.

The amount of the catalyst to be used in the disproportionation reaction can be properly adjusted according to the composition of the raw material to be used, the concentration of the raw material, the reaction temperature, the kind of the organic solvent, and the like. If the amount is excessively small, it is disadvantageous from the viewpoint of productivity. If the amount is excessively large, problems may arise in stirring or the like. Accordingly, it is preferable that the amount of the catalyst to be used based on 1 L of the reaction solvent be 1 to 500 g/L.

In the reaction solution after completion of the reaction in the disproportionation reaction, the catalyst, the diester of sugar and fatty acid, sugar, and unreacted monoester of sugar and fatty acid (or monoester of sugar and fatty acid generated in the equilibrium reaction) in some cases are contained. In the case where a low polar solvent is used as the reaction solvent, the diester of sugar and fatty acid (or a mixture of the diester of sugar and fatty acid and the monoester of sugar and fatty acid) can be obtained, for example, by separating the solid catalyst and sugar from the reaction solution by a standard solid liquid separation method, and distilling the reaction solvent away.

In the case where a polar solvent is used as the reaction solvent, the diester of sugar and fatty acid (or mixture of the diester of sugar and fatty acid and the monoester of sugar and fatty acid) can be obtained, for example, by adding the low polar solvent to the reaction solution to deposit the sugar, separating the solid catalyst and the deposited sugar from the reaction solution by a standard solid liquid separation method, and distilling the reaction solvent and the added low polar solvent away.

The catalyst recovered from the reaction solution can be reused as it is for the disproportionation reaction. In the case where the catalyst is repeatedly used for the disproportionation reaction and degraded, the catalyst can be activated by removing impurities such as a coloring substance adhering to the catalyst by a standard solvent washing, an oxidation treatment, a burning treatment, or the like.

The reaction solution after the catalyst and sugar are separated therefrom is usually colorless and transparent. In the case where coloring occurs, decolorization is performed on the catalyst by a standard bleaching treatment using a hydrogen peroxide solution or hypochlorous acid; a decolorizing treatment using an adsorbent such as activated carbon, ion exchange resin, and active alumina; or the like, and distilling the reaction solvent and the like away.

The reaction mode of the disproportionation reaction is not particularly limited, and a batch reaction mode using a standard stirring tank; a semi-batch reaction mode while necessary raw materials are added; a continuous reaction mode in which the catalyst is molded into a shape having a constant particle size or more, fixing the catalyst inside of a stirring tank or a tubular reactor, and performing addition of the necessary raw materials and extraction of the reaction product at the same time; and the like can be used.

The reaction conversion rate of the monoester of sugar and fatty acid in the disproportionation reaction can be properly adjusted according to the reaction temperature, the reaction time, the amount of the catalyst to be used, and the like. A preferable reaction conversion rate depends on the composition of the raw material, physical properties such as the interface activity demanded of the target product, and the like, but usually, it is preferable that conversion be performed at an extent in which the interface activity of the raw material is compared with that of the product and can be distinguished therefrom. It is needless to say that the reaction conversion rate is limited to the equilibrium conversion rate or less that is determined by the raw material composition, the reaction condition, and the like. It is preferred that the reaction conversion rate of the monoester of sugar and fatty acid be 10% or more, it is more preferred that the reaction conversion rate of the monoester of sugar and fatty acid be 25% or more, and it is still more preferred that the reaction conversion rate of the monoester of sugar and fatty acid be 40% or more.

(About Ester of Sugar Alcohol and Fatty Acid)

Esters of sugar alcohol and fatty acid, which are condensates of sugar alcohol and fatty acid, are widely used as nonionic surfactants added to foods, cosmetics, pharmaceuticals, detergents for kitchen, and the like because an ester of sugar alcohol and fatty acid has a remarkable interface activity, good biodegradability and safety, and the like.

As the industrial production method for an ester of sugar alcohol and fatty acid, a method for heating a sugar alcohol and a fatty acid in the presence of a catalyst or in the absence of a catalyst, and the like are known. Patent Literature 1 reports a method for producing an ester of sugar alcohol and fatty acid wherein a sugar alcohol having 4 to 6 carbon atoms and a lower alcohol ester of a fatty acid are subjected to a transesterification reaction in the presence of an alkali metal salt.

In the above industrial production method, however, dehydration condensation with sugar alcohol and fatty acid can be performed to obtain the ester of sugar alcohol and fatty acid while the selectivity of the diester is remarkably low, and a complex refining operation is needed to obtain the diester in a high concentration.

Moreover, in the method described in Patent Literature 1, it is also difficult to selectively synthesize the diester. When an attempt is made to obtain an ester of sugar alcohol and fatty acid with a high ratio of the diester, generation of the triester is difficult to avoid.

In contrast, according to the production method according to the present embodiment, the diester of sugar alcohol and fatty acid can be obtained with high selectivity.

Examples of the sugar alcohol constituting the monoester of sugar alcohol and fatty acid include glycerol, erythritol, threitol, arabinitol, xylitol, ribitol, iditol, galactitol, glucitol, mannitol, volemitol, perseitol, quercitol, and inositol. The sugar alcohol is not particularly limited in stereochemistry, and may be a single stereoisomer or a mixture of stereoisomers. As stereoisomers of inositol, myo-inositol (myo-inositol) is suitably used, for example.

The monoester of sugar alcohol and fatty acid may be prepared by any method. For example, the monoester of sugar alcohol and fatty acid can be prepared by: 1) a method for directly performing esterification using a fatty acid chloride or an anhydrous fatty acid and a sugar alcohol as raw materials, 2) a method for performing ester exchange using a fatty acid ester and a sugar alcohol as raw materials in which the fatty acid ester is a condensate of an alcohol having a small number of carbon atoms and a fatty acid, 3) a method using an enzyme such as lipase as a catalyst, and 4) a fermentation method using a microorganism.

For the raw material used in the disproportionation reaction, the monoester of sugar alcohol and fatty acid can be used alone, or a mixture of the monoester of sugar alcohol and fatty acid and the diester of sugar alcohol and fatty acid can be used. Moreover, the mixture further containing the triester of sugar alcohol and fatty acid, the tetraester of sugar alcohol and fatty acid, and the like can also be used as raw materials.

Namely, for example, when a mixture of the monoester of sugar alcohol and fatty acid and the diester of sugar alcohol and fatty acid is obtained as a reaction product resulted from the condensation reaction of a sugar alcohol with a fatty acid, the monoester of sugar alcohol and fatty acid can be isolated from the mixture and fed to the disproportionation reaction, or the mixture can be fed as it is to the disproportionation reaction.

Because the specific catalyst is used in the disproportionation reaction in the production method according to the present embodiment as described above, the successive reaction from the diester of sugar alcohol and fatty acid to the triester of sugar alcohol and fatty acid or tetraester of sugar alcohol and fatty acid hardly occurs. For this reason, even if the diester of sugar alcohol and fatty acid is mixed in the raw material, a by-product such as a triester of sugar alcohol and fatty acid is hardly produced, and the diester of sugar alcohol and fatty acid can be obtained with high selectivity.

The disproportionation reaction can be performed, for example, by keeping the reaction solution at a predetermined reaction temperature, the reaction solution being prepared by dissolving and/or dispersing the catalyst and the monoester of sugar alcohol and fatty acid in the reaction solvent.

The amount of the monoester of sugar alcohol and fatty acid in the reaction solution is not particularly limited, and can be properly adjusted according to saturated solubility in the reaction solvent, for example. Reactivity and productivity can be further improved, for example, by dissolving the monoester of sugar alcohol and fatty acid in the reaction solution near to the saturated solubility.

The monoester of sugar alcohol and fatty acid may not always be dissolved in the reaction solution. For example, the monoester of sugar alcohol and fatty acid may be fed into the reaction solution beyond the saturated solubility. In this case, the reaction is the reaction in the so-called slurry state, in which a solid monoester of sugar alcohol and fatty acid exists in the initial period of the reaction. Even in such a case, the disproportionation reaction progresses. As the disproportionation reaction progresses, the monoester of sugar alcohol and fatty acid gradually dissolves, and is converted into the diester of sugar alcohol and fatty acid until the equilibrium point is finally reached.

The reaction solvent may be solvents that do not inhibit the disproportionation reaction (transesterification reaction), and various organic solvents, ionic liquids, and supercritical fluids can be used. Examples of the organic solvents include ether compounds such as dimethyl ether, diethyl ether, methyl ethyl ether, 1,2-dimethoxyethane, and ethylene glycol dimethyl ether; ketone compounds such as acetone, methyl ethyl ketone, diethyl ketone, dipropyl ketone, dibutyl ketone, methyl isobutyl ketone, and 2,4-pentanedione; nitrile compounds such as acetonitrile, acrylonitrile, propionitrile, adiponitrile, and isobutyronitrile; halogenated alkyl compounds such as chloroform, methylene chloride, carbon tetrachloride, and 1,2-dichloroethane; tertiary alcohol compounds such as tert-butyl alcohol; amide compounds such as dimethyl formamide and dimethyl acetoamide; amine compounds such as ethylenediamine and hexamethylenediamine; and sulfoxide compounds such as dimethyl sulfoxide. Examples of the ionic liquids include imidazolium compounds, pyridinium compounds, quaternary ammonium compounds, and phosphonium compounds, and specifically include 1-butyl-3-methylimidazolium hexafluorophosphate and 1-butyl-3-methylimidazolium tetrafluoroborate. Examples of the supercritical fluids include supercritical carbon dioxide.

It is preferable that the reaction solvent from which the water content is removed as much as possible by performing a dehydration treatment or the like be used. A very small amount of water causes no problem, but if the content of water is larger, a hydrolysis reaction in addition to the disproportionation reaction (transesterification reaction) competes. As a result, a fatty acid is easily produced as a by-product. If the fatty acid is produced as a by-product, separation and refining of the diester of sugar alcohol and fatty acid may be difficult.

For the reaction temperature, 35 to 100° C. is preferred, 50 to 90° C. is more preferred, and 50 to 75° C. is still more preferred. If the reaction temperature is within this range, reactivity and productivity are remarkably improved. If the reaction temperature is excessively low, reactivity and productivity tend to be difficult to improve. If the reaction temperature is excessively high, reactivity and productivity may reduce. The cause for reactivity and productivity to reduce by increasing the reaction temperature is not clear, but it is thought that degradation of the catalyst due to a high temperature occurs, or catalyst activity is inhibited.

The reaction pressure in the disproportionation reaction is not particularly limited, and may be atmospheric pressure. The composition of the gaseous phase portion in the disproportionation reaction is not particularly limited. Usually, an inert gas such as nitrogen is selected from the viewpoints of safety such as prevention of explosion and suppression of the oxidation reaction.

The disproportionation reaction can be performed until the reaction reaches the equilibrium point at which apparent generation of the diester of sugar alcohol and fatty acid stops. The time to reach the equilibrium point varies according to the composition of the raw material to be used, the concentration of the raw material, the reaction temperature, the concentration of the catalyst, the kind of the reaction solvent, and the like. The reaction time can be 1 to 72 hours, for example.

The amount of the catalyst to be used in the disproportionation reaction can be properly adjusted according to the composition of the raw material to be used, the concentration of the raw material, the reaction temperature, the kind of the organic solvent, and the like. If the amount is excessively small, it is disadvantageous from the viewpoint of productivity. If the amount is excessively large, problems may arise in stirring or the like. Accordingly, it is preferable that the amount of the catalyst to be used based on 1 L of the reaction solvent be 1 to 500 g/L.

The catalyst, the diester of sugar alcohol and fatty acid, the sugar alcohol, and the unreacted monoester of sugar alcohol and fatty acid (or monoester of sugar alcohol and fatty acid generated in the equilibrium reaction) in some cases are contained in the reaction solution after completion of the reaction in the disproportionation reaction. In the case where a low polar solvent is used as the reaction solvent, the diester of sugar alcohol and fatty acid (or a mixture of the diester of sugar alcohol and fatty acid and the monoester of sugar alcohol and fatty acid) can be obtained, for example, by separating a solid catalyst and sugar alcohol from the reaction solution by a standard solid liquid separation method, and distilling the reaction solvent away.

In the case where a polar solvent is used as the reaction solvent, the diester of sugar alcohol and fatty acid (or a mixture of the diester of sugar alcohol and fatty acid and the monoester of sugar alcohol and fatty acid) can be obtained, for example, by adding the low polar solvent to the reaction solution to deposit sugar alcohol, separating the solid catalyst and the deposited sugar alcohol from the reaction solution by a standard solid liquid separation method, and distilling the reaction solvent and the added low polar solvent away.

The catalyst recovered from the reaction solution can be reused as it is for the disproportionation reaction. In the case where the catalyst is repeatedly used for the disproportionation reaction and degraded, the catalyst can be activated by removing impurities such as a coloring substance adhering to the catalyst by a standard solvent washing, an oxidation treatment, a burning treatment, or the like.

The reaction solution after the catalyst and sugar alcohol are separated therefrom is usually colorless and transparent. In the case where coloring occurs, decolorization is performed on the catalyst by a standard bleaching treatment using a hydrogen peroxide solution or hypochlorous acid; a decolorizing treatment using an adsorbent such as activated carbon, ion exchange resin, and active alumina; or the like, and distilling the reaction solvent and the like away.

The reaction mode of the disproportionation reaction is not particularly limited, and a batch reaction mode using a standard stirring tank; a semi-batch reaction mode while necessary raw materials are added; a continuous reaction mode in which the catalyst is molded into a shape having a constant particle size or more, fixing the catalyst inside of a stirring tank or a tubular reactor, and performing addition of the necessary raw materials and extraction of the reaction product at the same time; and the like can be used.

The reaction conversion rate of the monoester of sugar alcohol and fatty acid in the disproportionation reaction can be properly adjusted according to the reaction temperature, the reaction time, the amount of the catalyst to be used, and the like. A preferable reaction conversion rate depends on the composition of the raw material, physical properties such as the interface activity demanded of the target product, and the like, but usually, it is preferable that conversion be performed at an extent in which the interface activity of the raw material is compared with that of the product and can be distinguished therefrom. It is needless to say that the reaction conversion rate is limited to the equilibrium conversion rate or less that is determined by the raw material composition, the reaction condition, and the like. It is preferred that the reaction conversion rate of the monoester of sugar alcohol and fatty acid be 10% or more, it is more preferred that the reaction conversion rate of the monoester of sugar alcohol and fatty acid be 15% or more, and it is still more preferred that the reaction conversion rate of the monoester of sugar alcohol and fatty acid be 20% or more.

As above, suitable embodiments according to the present invention have been described, the present invention will not be limited to the above embodiments. For example, in the embodiments, the method for producing a diester of polyhydric alcohol and fatty acid from a monoester of polyhydric alcohol and fatty acid has been described, but the present invention can also be a method wherein various methods for synthesizing a monoester of polyhydric alcohol and fatty acid (or a mixture of a monoester of polyhydric alcohol and fatty acid and a diester of polyhydric alcohol and fatty acid) using a fatty acid or a fatty acid derivative (such as fatty acid methyl) and polyhydric alcohol as raw materials are combined, and resultantly a diester of polyhydric alcohol and fatty acid is produced using a fatty acid or a fatty acid derivative and a polyhydric alcohol as raw materials.

EXAMPLES

Hereinafter, the present invention will be more specifically described based on Examples, but the present invention will not be limited to Examples, and various changes and modifications can be made without departing from the scope of the invention.

The products obtained in Production Examples and Comparative Examples were analyzed by the following method.

(GPC Analysis)

By GPC analysis of the product, the contents of the monoester of polyhydric alcohol and fatty acid, the diester of polyhydric alcohol and fatty acid, the triester of polyhydric alcohol and fatty acid, the tetraester of polyhydric alcohol and fatty acid, fatty acid methyl, and fatty acid in the products were measured. Specifically, measurement was performed using a gel permeation chromatography (GPC) (LC-10Avp made by SHIMADZU Corporation) in which the column was a GPC column (TSK-GEL G2500HXL made by Tosoh Corporation (7.8 mmID×30 cmL×two columns in series)), the column temperature was 40° C., the mobile phase was THF, the flow rate was 0.5 mL/min, the detector was RI (RID-6A made by SHIMADZU Corporation), and the injection amount was 10 μL.

(Evaluation of Interface Activity)

Evaluation of the interface activity of the product was performed as follows. Namely, the critical micelle concentration (cmc) and surface tension in formation of the critical micelle (γcmc) each were measured with an automatic surface tension meter (made by Kyowa Interface Science Co., Ltd., CBVP-Z type). The measurement temperature was 25° C., and samples were prepared with 0.001 to 0.5% by mass aqueous solutions.

Production Example A-1

Preparation of Glucose Lauric Acid Monoester

Glucose lauric acid monoester was prepared by the following method. Namely, 33 mmol of methyl laurate (made by Wako Pure Chemical Industries, Ltd.), 132 mmol of D-glucose (made by Wako Pure Chemical Industries, Ltd.), 100 mL of dimethyl sulfoxide (made by Wako Pure Chemical Industries, Ltd.), and 0.12 g of potassium carbonate, anhydrous were charged into a 200 mL three-necked flask. The flask was immersed in an oil bath at 90° C., and the reaction was made under a reduced pressure of 17 mmHg for 3 hours by stirring with a stirrer.

The obtained reaction solution was cooled, and diluted 5 times with ethylene glycol dimethyl ether to deposit the unreacted glucose. Then, a solid product (potassium carbonate, anhydrous, glucose) was filtered by filtering under reduced pressure, and the solvent was distilled away with an evaporator to obtain a condensed dried solid product. Next, the target product was deposited with n-heptane. Then, the unreacted fatty acid was filtered out by filtering under reduced pressure, and the obtained product was further dried under reduced pressure to obtain the target product, glucose lauric acid monoester, as a solid.

GPC analysis was performed on the obtained glucose lauric acid monoester. The purity of the glucose lauric acid monoester was 96% in molar ratio.

Production Example A-2

Preparation of Glucose Adipic Acid Monoester

Glucose adipic acid monoester was prepared by the same method as that in Production Example A-1 except that 33 mmol of methyl adipate was used instead of methyl laurate. GPC analysis was performed on the obtained glucose adipic acid monoester. The purity of glucose adipic acid monoester was 97% in molar ratio.

Production Example A-3

Preparation of Glucose Caprylic Acid Monoester

Glucose caprylic acid monoester was prepared by the same method as that in Production Example A-1 except that 33 mmol of methyl caprylate was used instead of methyl laurate. GPC analysis was performed on the obtained glucose caprylic acid monoester. The purity of glucose caprylic acid monoester was 98% in molar ratio.

Production Example A-4

Preparation of Glucose Pelargonic Acid Monoester

Glucose pelargonic acid monoester was prepared by the same method as that in Production Example A-1 except that 33 mmol of methyl pelargonate was used instead of methyl laurate. GPC analysis was performed on the obtained glucose pelargonic acid monoester. The purity of glucose pelargonic acid monoester was 97% in molar ratio.

Production Example A-5

Preparation of Glucose Capric Acid Monoester

Glucose capric acid monoester was prepared by the same method as that in Production Example A-1 except that 33 mmol of methyl caprate was used instead of methyl laurate. GPC analysis was performed on the obtained glucose capric acid monoester. The purity of glucose capric acid monoester was 96% in molar ratio.

Production Example A-6

Preparation of Glucose Pentadecylic Acid Monoester

Glucose pentadecylic acid monoester was prepared by the same method as that in Production Example A-1 except that 33 mmol of methyl pentadecylate was used instead of methyl laurate. GPC analysis was performed on the obtained glucose pentadecylic acid monoester. The purity of glucose pentadecylic acid monoester was 97% in molar ratio.

Production Example A-7

Preparation of Glucose Palmitic Acid Monoester

Glucose palmitic acid monoester was prepared by the same method as that in Production Example A-1 except that 33 mmol of methyl palmitate was used instead of methyl laurate. GPC analysis was performed on the obtained glucose palmitic acid monoester. The purity of glucose palmitic acid monoester was 96% in molar ratio.

Production Example A-8

Preparation of Glucose Dodecanedioic Acid Monoester 120 mmol of lauric acid (made by Wako Pure Chemical Industries, Ltd.), 120 mmol of D-glucose (made by Wako Pure Chemical Industries, Ltd.), 150 mL of acetone (made by Wako Pure Chemical Industries, Ltd.), 6.0 g of immobilized Lipase (NovozymeSP435), and 30 g of a molecular sieve 4A (made by Wako Pure Chemical Industries, Ltd.) were charged into a 300 mL three-necked flask. The flask was immersed in a water bath at 50° C., and the reaction was made for 48 hours by stirring with a stirrer.

The obtained reaction solution was cooled, and diluted 20 times with ethylene glycol dimethyl ether to deposit the unreacted glucose. Then, a solid product (Lipase, molecular sieve 4A, and glucose) was filtered by filtering under reduced pressure, and the solvent was distilled away with an evaporator to obtain a condensed dried solid product. Next, the target product was deposited with hexyl acetate. Then, the unreacted fatty acid was filtered out by filtering under reduced pressure, and the obtained product was further dried under reduced pressure to obtain the target product, glucose dodecanedioic acid monoester, as a solid. GPC analysis was performed on the obtained glucose dodecanedioic acid monoester. The purity of glucose dodecanedioic acid monoester was 96% in molar ratio.

Production Example A-9

Preparation of Fructose Lauric Acid Monoester

Fructose lauric acid monoester was prepared by the same method as that in Production Example A-1 except that 132 mmol of fructose was used instead of D-glucose. GPC analysis was performed on the obtained fructose lauric acid monoester. The purity of fructose lauric acid monoester was 97% in molar ratio.

Production Example A-10

Preparation of Galactose Lauric Acid Monoester

Galactose lauric acid monoester was prepared by the same method as that in Production Example A-1 except that 132 mmol of galactose was used instead of D-glucose. GPC analysis was performed on the obtained galactose lauric acid monoester. The purity of galactose lauric acid monoester was 98% in molar ratio.

Example A-1

The disproportionation reaction was performed using glucose lauric acid monoester prepared in Production Example A-1 as the raw material and commercially available $Mg_6Al_2(OH)_{16}CO_3 \cdot zH_2O$ as the catalyst. Specifically, 0.037 g of glucose lauric acid monoester, 0.04 g of the catalyst, and 1 mL of 1,2-dimethoxyethane as the reaction solvent were charged into a 2 mL screw cap tube bottle, and the reaction was made at the reaction temperature of 60° C. for 24 hours using a thermostat shaking incubator.

After the reaction was completed, the reaction solution was diluted approximately 5 times with 1,2-dimethoxyethane, and the catalyst and glucose were removed by filtering with a 0.2 μm filter made of PTFE to obtain a glucose lauric acid ester mixture. GPC analysis was performed on part of the obtained mixture. The glucose lauric acid monoester conversion rate was 30%, and the glucose lauric acid diester selectivity was 100%. The monoester conversion rate can be determined by the following formula (a), and the diester selectivity can be determined by the following formula (b).

monoester conversion rate (%)=(raw material monoester (mol)−unreacted monoester (mol))/ raw material monoester (mol)    (a)

diester selectivity (%)=generated diester (mol)/total amount (mol) of generated diester, triester, and tetraester    (b)

Example A-2

A glucose lauric acid ester mixture was obtained in the same manner as in Example A-1 except that the reaction time was 48 hours. GPC analysis was performed on part of the obtained mixture. The glucose lauric acid monoester conversion rate was 75%, and the glucose lauric acid diester selectivity was 100%. The molar ratio of glucose lauric acid diester to glucose lauric acid monoester in the obtained mixture (diester:monoester) was 4:6.

Figure 1:
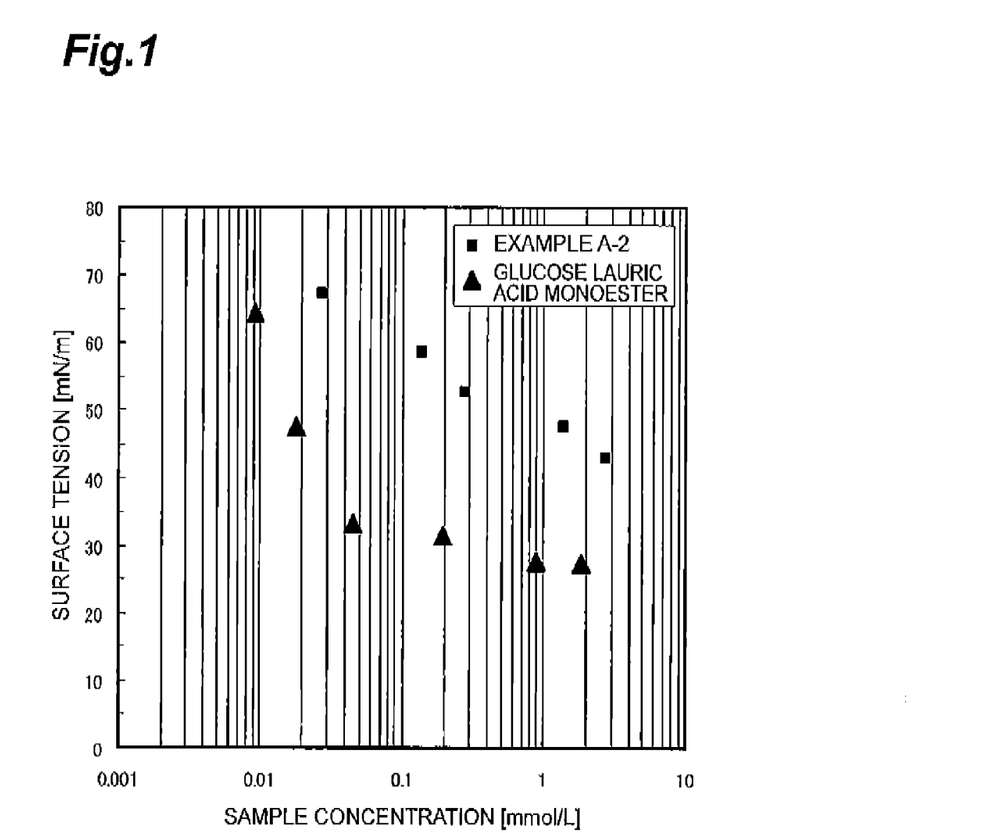
FIG. 1 is a diagram showing results of evaluation of the interface activity of a glucose lauric acid ester mixture obtained in Example A-2.

Evaluation of interface activity was performed on the obtained mixture by the above method, and it was found out that the mixture had values of cmc=$5 \times 10^{-5}$ [M] and γcmc=33 [mN/m] and high interface activity. Evaluation of interface activity was also performed on glucose lauric acid monoester in the same manner, and cmc=$1 \times 10^{-3}$ [M] and γcmc=46 [mN/ m]. The results of evaluation of interface activity of the mixture and glucose lauric acid monoester in Example A-2 are shown in FIG. 1.

Moreover, n-heptane was added to the obtained mixture to deposit glucose lauric acid monoester. Then, the solid product was filtered out by filtering under reduced pressure, and the solvent was distilled away with an evaporator to obtain glucose lauric acid diester as a solid. GPC analysis was performed on the obtained glucose lauric acid diester. The purity of glucose lauric acid diester was 100% in molar ratio.

Example A-3

A glucose lauric acid ester mixture was obtained by the same method as that in Example A-1 except that the amount of the catalyst to be used was 0.12 g and the reaction time was 3 hours. GPC analysis was performed on part of the obtained mixture. The glucose lauric acid monoester conversion rate was 28%, and the glucose lauric acid diester selectivity was 100%.

Example A-4

A glucose lauric acid ester mixture was obtained by the same method as that in Example A-1 except that the amount of the catalyst to be used was 0.12 g and the reaction time was 7 hours. GPC analysis was performed on part of the obtained mixture. The glucose lauric acid monoester conversion rate was 42%, and the glucose lauric acid diester selectivity was 100%.

Example A-5

A glucose lauric acid ester mixture was obtained by the same method as that in Example A-1 except that the amount of the catalyst to be used was 0.4 g and the reaction time was 3 hours. GPC analysis was performed on part of the obtained mixture. The glucose lauric acid monoester conversion rate was 36%, and the glucose lauric acid diester selectivity was 100%.

Example A-6

A glucose lauric acid ester mixture was obtained by the same method as that in Example A-1 except that the amount of the catalyst to be used was 0.4 g and the reaction time was 7 hours. GPC analysis was performed on part of the obtained mixture. The glucose lauric acid monoester conversion rate was 49%, and the glucose lauric acid diester selectivity was 100%.

Example A-7

A glucose lauric acid ester mixture was obtained by the same method as that in Example A-1 except that 0.04 g of commercially available $Mg_4Al_2(OH)_{12}Cl_2 \cdot zH_2O$ was used as the catalyst. GPC analysis was performed on part of the obtained mixture. The glucose lauric acid monoester conversion rate was 32%, and the glucose lauric acid diester selectivity was 100%.

Example A-8

A glucose lauric acid ester mixture was obtained by the same method as that in Example A-1 except that 0.04 g of commercially available $Mg_4Al_2(OH)_{12}CO_3 \cdot zH_2O$ was used as the catalyst. GPC analysis was performed on part of the obtained mixture. The glucose lauric acid monoester conversion rate was 31%, and the glucose lauric acid diester selectivity was 100%.

Example A-9

A glucose lauric acid ester mixture was obtained by the same method as that in Example A-1 except that 0.04 g of commercially available $Mg_{10}Al_2(OH)_{24}Cl_2 \cdot zH_2O$ was used as the catalyst. GPC analysis was performed on part of the obtained mixture. The glucose lauric acid monoester conversion rate was 28%, and the glucose lauric acid diester selectivity was 100%.

Example A-10

A glucose lauric acid ester mixture was obtained by the same method as that in Example A-1 except that 0.04 g of commercially available $Mg_{10}Al_2(OH)_{24}CO_3 \cdot zH_2O$ was used as the catalyst. GPC analysis was performed on part of the obtained mixture. The glucose lauric acid monoester conversion rate was 25%, and the glucose lauric acid diester selectivity was 100%.

Example A-11

A glucose lauric acid ester mixture was obtained by the same method as that in Example A-1 except that 0.04 g of commercially available $Ca_3Al_2(OH)_{10}Cl_2 \cdot zH_2O$ was used as the catalyst. GPC analysis was performed on part of the obtained mixture. The glucose lauric acid monoester conversion rate was 26%, and the glucose lauric acid diester selectivity was 100%.

Example A-12

A glucose lauric acid ester mixture was obtained by the same method as that in Example A-1 except that 0.04 g of commercially available $Ca_4Al_2(OH)_{10}Cl_2 \cdot zH_2O$ was used as the catalyst. GPC analysis was performed on part of the obtained mixture. The glucose lauric acid monoester conversion rate was 24%, and the glucose lauric acid diester selectivity was 100%.

Example A-13

A glucose lauric acid ester mixture was obtained by the same method as that in Example A-1 except that 0.04 g of commercially available $Ca_4Mg_6Al_5(OH)_{10}Cl_2 \cdot zH_2O$ was used as the catalyst. GPC analysis was performed on part of the obtained mixture. The glucose lauric acid monoester conversion rate was 25%, and the glucose lauric acid diester selectivity was 100%.

Reaction conditions in Examples A-1 to A-13 and results of analysis of the obtained mixtures are shown in Table 2.

TABLE 2

| | Catalyst | | | Mono- | |
|---|---|---|---|---|---|
| | Kind | Amount to be added (g) | Reaction time (hours) | ester conversion rate (%) | Diester selectivity (%) |
| Example A-1 | $Mg_6Al_2(OH)_{16}CO_3 \cdot zH_2O$ | 0.04 | 24 | 30 | 100 |
| Example A-2 | $Mg_6Al_2(OH)_{16}CO_3 \cdot zH_2O$ | 0.04 | 48 | 75 | 100 |

TABLE 2-continued

| Kind | Catalyst Amount to be added (g) | Reaction time (hours) | Monoester conversion rate (%) | Diester selectivity (%) |
|---|---|---|---|---|
| Example A-3 | $Mg_6Al_2(OH)_{16}CO_3 \cdot zH_2O$ | 0.12 | 3 | 28 | 100 |
| Example A-4 | $Mg_6Al_2(OH)_{16}CO_3 \cdot zH_2O$ | 0.12 | 7 | 42 | 100 |
| Example A-5 | $Mg_6Al_2(OH)_{16}CO_3 \cdot zH_2O$ | 0.4 | 3 | 36 | 100 |
| Example A-6 | $Mg_6Al_2(OH)_{16}CO_3 \cdot zH_2O$ | 0.4 | 7 | 49 | 100 |
| Example A-7 | $Mg_4Al_2(OH)_{12}Cl_2 \cdot zH_2O$ | 0.04 | 24 | 32 | 100 |
| Example A-8 | $Mg_4Al_2(OH)_{12}CO_3 \cdot zH_2O$ | 0.04 | 24 | 31 | 100 |
| Example A-9 | $Mg_{10}Al_2(OH)_{24}Cl_2 \cdot zH_2O$ | 0.04 | 24 | 28 | 100 |
| Example A-10 | $Mg_{10}Al_2(OH)_{24}CO_3 \cdot zH_2O$ | 0.04 | 24 | 25 | 100 |
| Example A-11 | $Ca_3Al_2(OH)_{10}Cl_2 \cdot zH_2O$ | 0.04 | 24 | 26 | 100 |
| Example A-12 | $Ca_4Al_2(OH)_{10}Cl_2 \cdot zH_2O$ | 0.04 | 24 | 24 | 100 |
| Example A-13 | $Ca_4Mg_6Al_6(OH)_{10}Cl_2 \cdot zH_2O$ | 0.04 | 24 | 25 | 100 |

Example A-14

A glucose lauric acid ester mixture was obtained by the same method as that in Example A-8 except that the reaction solvent was changed from 1,2-dimethoxyethane to diethylene glycol. GPC analysis was performed on part of the obtained mixture. The glucose lauric acid monoester conversion rate was 31%, and the glucose lauric acid diester selectivity was 100%.

Example A-15

A glucose lauric acid ester mixture was obtained by the same method as that in Example A-8 except that the reaction solvent was changed from 1,2-dimethoxyethane to acetone. GPC analysis was performed on part of the obtained mixture. The glucose lauric acid monoester conversion rate was 37%, and the glucose lauric acid diester selectivity was 100%.

Example A-16

A glucose lauric acid ester mixture was obtained by the same method as that in Example A-8 except that the reaction solvent was changed from 1,2-dimethoxyethane to diethyl ketone. GPC analysis was performed on part of the obtained mixture. The glucose lauric acid monoester conversion rate was 20%, and the glucose lauric acid diester selectivity was 100%.

Example A-17

A glucose lauric acid ester mixture was obtained by the same method as that in Example A-8 except that the reaction solvent was changed from 1,2-dimethoxyethane to dipropyl ketone. GPC analysis was performed on part of the obtained mixture. The glucose lauric acid monoester conversion rate was 24%, and the glucose lauric acid diester selectivity was 100%.

Example A-18

A glucose lauric acid ester mixture was obtained by the same method as that in Example A-8 except that the reaction solvent was changed from 1,2-dimethoxyethane to dibutyl ketone. GPC analysis was performed on part of the obtained mixture. The glucose lauric acid monoester conversion rate was 22%, and the glucose lauric acid diester selectivity was 100%.

Example A-19

A glucose lauric acid ester mixture was obtained by the same method as that in Example A-8 except that the reaction solvent was changed from 1,2-dimethoxyethane to acetonitrile. GPC analysis was performed on part of the obtained mixture. The glucose lauric acid monoester conversion rate was 38%, and the glucose lauric acid diester selectivity was 100%.

Example A-20

A glucose lauric acid ester mixture was obtained by the same method as that in Example A-8 except that the reaction solvent was changed from 1,2-dimethoxyethane to chloroform. GPC analysis was performed on part of the obtained mixture. The glucose lauric acid monoester conversion rate was 25%, and the glucose lauric acid diester selectivity was 100%.

Example A-21

A glucose lauric acid ester mixture was obtained by the same method as that in Example A-8 except that the reaction solvent was changed from 1,2-dimethoxyethane to hexamethylenediamine. GPC analysis was performed on part of the obtained mixture. The glucose lauric acid monoester conversion rate was 38%, and the glucose lauric acid diester selectivity was 100%.

Example A-22

A glucose lauric acid ester mixture was obtained by the same method as that in Example A-8 except that the reaction solvent was changed from 1,2-dimethoxyethane to dimethyl sulfoxide. GPC analysis was performed on part of the obtained mixture. The glucose lauric acid monoester conversion rate was 37%, and the glucose lauric acid diester selectivity was 100%.

Example A-23

A glucose lauric acid ester mixture was obtained by the same method as that in Example A-8 except that the reaction solvent was changed from 1,2-dimethoxyethane to n-hexane. GPC analysis was performed on part of the obtained mixture. The glucose lauric acid monoester conversion rate was 28%, and the glucose lauric acid diester selectivity was 100%.

Example A-24

A glucose lauric acid ester mixture was obtained by the same method as that in Example A-8 except that the reaction solvent was changed from 1,2-dimethoxyethane to n-heptane. GPC analysis was performed on part of the obtained mixture. The glucose lauric acid monoester conversion rate was 23%, and the glucose lauric acid diester selectivity was 100%.

Example A-25

A glucose lauric acid ester mixture was obtained by the same method as that in Example A-8 except that the reaction solvent was changed from 1,2-dimethoxyethane to n-octane. GPC analysis was performed on part of the obtained mixture. The glucose lauric acid monoester conversion rate was 6%, and the glucose lauric acid diester selectivity was 100%.

The reaction conditions in Examples A-8 and A-14 to A-25 and the results of analysis of the obtained mixtures are shown in Table 3.

TABLE 3

|  | Kind of reaction solvent | Reaction time (hours) | Monoester conversion rate (%) | Diester selectivity (%) |
| --- | --- | --- | --- | --- |
| Example A-8 | 1,2-Dimethoxyethane | 24 | 31 | 100 |
| Example A-14 | Diethylene glycol | 24 | 31 | 100 |
| Example A-15 | Acetone | 24 | 37 | 100 |
| Example A-16 | Diethyl ketone | 24 | 20 | 100 |
| Example A-17 | Dipropyl ketone | 24 | 24 | 100 |
| Example A-18 | Dibutyl ketone | 24 | 22 | 100 |
| Example A-19 | Acetonitrile | 24 | 38 | 100 |
| Example A-20 | Chloroform | 24 | 25 | 100 |
| Example A-21 | Hexamethylenediamine | 24 | 38 | 100 |
| Example A-22 | Dimethyl sulfoxide | 24 | 37 | 100 |
| Example A-23 | n-Hexane | 24 | 28 | 100 |
| Example A-24 | n-Heptane | 24 | 23 | 100 |
| Example A-25 | n-Octane | 24 | 6 | 100 |

Example A-26

A glucose adipic acid ester mixture was obtained by the same method as that in Example A-1 except that 0.037 g of glucose adipic acid monoester was used as the raw material and 0.04 g of commercially available $Ca_4Al_2(OH)_{10}Cl_2 \cdot zH_2O$ was used as the catalyst. GPC analysis was performed on part of the obtained mixture. The glucose adipic acid monoester conversion rate was 15%, and the glucose adipic acid diester selectivity was 100%.

Example A-27

A glucose caprylic acid ester mixture was obtained by the same method as that in Example A-1 except that 0.037 g of glucose caprylic acid monoester was used as the raw material and 0.04 g of commercially available $Ca_4Al_2(OH)_{10}Cl_2 \cdot zH_2O$ was used as the catalyst. GPC analysis was performed on part of the obtained mixture. The glucose caprylic acid monoester conversion rate was 9%, and the glucose caprylic acid diester selectivity was 100%.

Example A-28

A glucose pelargonic acid ester mixture was obtained by the same method as that in Example A-1 except that 0.037 g of glucose pelargonic acid monoester was used as the raw material and 0.04 g of commercially available $Ca_4Al_2(OH)_{10}Cl_2 \cdot zH_2O$ was used as the catalyst. GPC analysis was performed on part of the obtained mixture. The glucose pelargonic acid monoester conversion rate was 12%, and the glucose pelargonic acid diester selectivity was 100%.

Example A-29

A glucose capric acid ester mixture was obtained by the same method as that in Example A-1 except that 0.037 g of glucose capric acid monoester was used as the raw material and 0.04 g of commercially available $Mg_4Al_2(OH)_{12}Cl_2 \cdot zH_2O$ was used as the catalyst. GPC analysis was performed on part of the obtained mixture. The glucose capric acid monoester conversion rate was 32%, and the glucose capric acid diester selectivity was 100%.

Example A-30

A glucose capric acid ester mixture was obtained by the same method as that in Example A-1 except that 0.037 g of glucose capric acid monoester was used as the raw material. GPC analysis was performed on part of the obtained mixture. The glucose capric acid monoester conversion rate was 30%, and the glucose capric acid diester selectivity was 100%.

Example A-31

A glucose pentadecylic acid ester mixture was obtained by the same method as that in Example A-1 except that 0.037 g of glucose pentadecylic acid monoester was used as the raw material and 0.04 g of commercially available $Mg_4Al_2(OH)_{12}Cl_2 \cdot zH_2O$ was used as the catalyst. GPC analysis was performed on part of the obtained mixture. The glucose pentadecylic acid monoester conversion rate was 25%, and the glucose pentadecylic acid diester selectivity was 100%.

Example A-32

A glucose pentadecylic acid ester mixture was obtained by the same method as that in Example A-1 except that 0.037 g of glucose pentadecylic acid monoester was used as the raw material. GPC analysis was performed on part of the obtained mixture. The glucose pentadecylic acid monoester conversion rate was 30%, and the glucose pentadecylic acid diester selectivity was 100%.

Example A-33

A glucose palmitic acid ester mixture was obtained by the same method as that in Example A-1 except that 0.037 g of glucose palmitic acid monoester was used as the raw material and 0.04 g of commercially available $Mg_4Al_2(OH)_{12}Cl_2 \cdot zH_2O$ was used as the catalyst. GPC analysis was performed on part of the obtained mixture. The glucose palmitic acid monoester conversion rate was 28%, and the glucose palmitic acid diester selectivity was 100%.

Example A-34

A glucose palmitic acid ester mixture was obtained by the same method as that in Example A-1 except that 0.037 g of glucose palmitic acid monoester was used as the raw material. GPC analysis was performed on part of the obtained mixture. The glucose palmitic acid monoester conversion rate was 32%, and the glucose palmitic acid diester selectivity was 100%.

Example A-35

A glucose dodecanedioic acid ester mixture was obtained by the same method as that in Example A-1 except that 0.037 g of glucose dodecanedioic acid monoester was used as the raw material. GPC analysis was performed on part of the obtained mixture. The glucose dodecanedioic acid monoester conversion rate was 26%, and the glucose dodecanedioic acid diester selectivity was 100%.

Example A-36

A fructose lauric acid ester mixture was obtained by the same method as that in Example A-1 except that 0.037 g of fructose lauric acid monoester was used as the raw material and 0.04 g of commercially available $Mg_4Al_2(OH)_{12}Cl_2 \cdot zH_2O$ was used as the catalyst. GPC analysis was performed on part of the obtained mixture. The fructose lauric acid monoester conversion rate was 23%, and the fructose lauric acid diester selectivity was 100%.

Example A-37

A fructose lauric acid ester mixture was obtained by the same method as that in Example A-1 except that 0.037 g of fructose lauric acid monoester was used as the raw material. GPC analysis was performed on part of the obtained mixture. The fructose lauric acid monoester conversion rate was 30%, and the fructose lauric acid diester selectivity was 100%.

Example A-38

A galactose lauric acid ester mixture was obtained by the same method as that in Example A-1 except that 0.037 g of galactose lauric acid monoester was used as the raw material and 0.04 g of commercially available $Mg_4Al_2(OH)_{12}Cl_2 \cdot zH_2O$ was used as the catalyst. GPC analysis was performed on part of the obtained mixture. The galactose lauric acid monoester conversion rate was 24%, and the galactose lauric acid diester selectivity was 100%.

Example A-39

A galactose lauric acid ester mixture was obtained by the same method as that in Example A-1 except that 0.037 g of galactose lauric acid monoester was used as the raw material. GPC analysis was performed on part of the obtained mixture. The galactose lauric acid monoester conversion rate was 32%, and the galactose lauric acid diester selectivity was 100%.

The reaction conditions in Examples A-26 to A-39 and the results of analysis of the obtained mixtures are shown in Table 4.

Examples A-40 to A-47

A glucose lauric acid ester mixture was obtained by the same method as that in Example A-1 except that the reaction temperature was 35° C. (Example A-40), 40° C. (Example A-41), 45° C. (Example A-42), 50° C. (Example A-43), 60° C. (Example A-44), 75° C. (Example A-45), 90° C. (Example A-46), and 100° C. (Example A-47), and the reaction time was 3 hours.

Figure 2:
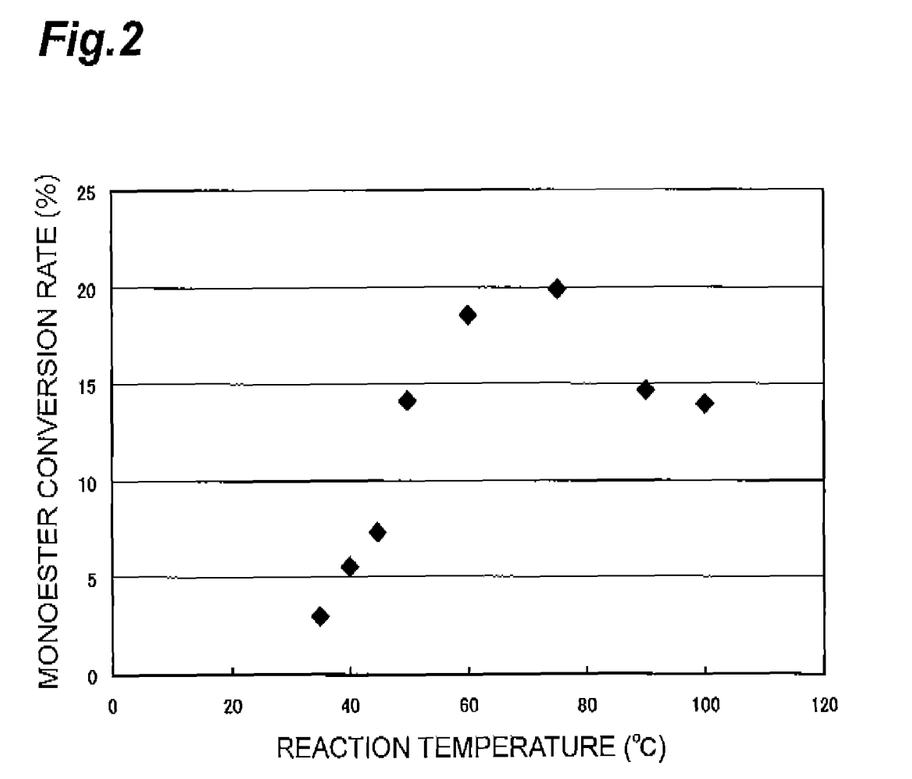
FIG. 2 is a diagram showing the relationship between the reaction temperature and the monoester conversion rate in the disproportionation reaction in Examples A-40 to A-47.

GPC analysis was performed on part of the respective mixtures obtained in Examples. The glucose lauric acid monoester conversion rate and the glucose lauric acid diester selectivity were as shown in Table 5. FIG. 2 is a diagram showing the relationship between the reaction temperature and the monoester conversion rate in the disproportionation reaction in Examples A-40 to A-47.

TABLE 5

| | Reaction temperature (° C.) | Monoester conversion rate (%) | Diester selectivity (%) |
|---|---|---|---|
| Example A-40 | 35 | 3 | 100 |
| Example A-41 | 40 | 6 | 100 |
| Example A-42 | 45 | 7 | 100 |
| Example A-43 | 50 | 14 | 100 |
| Example A-44 | 60 | 19 | 100 |
| Example A-45 | 75 | 20 | 100 |
| Example A-46 | 90 | 15 | 100 |
| Example A-47 | 100 | 14 | 100 |

Comparative Example A-1

The catalyst in Example A-1 was replaced by an inorganic oxide having no hydrotalcite structure $Mg_6Al_2O_9$, and the reaction was performed, but the disproportionation reaction did not progress at all.

Production Example B-1

Preparation of Inositol Capric Acid Monoester 11 mmol of methyl caprate (made by Wako Pure Chemical Industries, Ltd.), 33 mmol of myo-inositol (made by Wako Pure Chemical Industries, Ltd.), 100 mL of dimethyl sulfoxide (made by Wako Pure Chemical Industries, Ltd.), and 0.30 g of potassium carbonate, anhydrous were charged into a 200 mL three-necked flask. The flask was immersed in an oil bath

TABLE 4

| | | Catalyst | | Monoester | Diester |
|---|---|---|---|---|---|
| | Raw material | Kind | Amount to be added (g) | conversion rate (%) | selectivity (%) |
| Example A-26 | Glucose adipic acid monoester | $Ca_4Al_2(OH)_{10}Cl_2 \cdot zH_2O$ | 0.04 | 15 | 100 |
| Example A-27 | Glucose caprylic acid monoester | $Ca_4Al_2(OH)_{10}Cl_2 \cdot zH_2O$ | 0.04 | 9 | 100 |
| Example A-28 | Glucose pelargonic acid monoester | $Ca_4Al_2(OH)_{10}Cl_2 \cdot zH_2O$ | 0.04 | 12 | 100 |
| Example A-29 | Glucose capric acid monoester | $Mg_4Al_2(OH)_{12}Cl_2 \cdot zH_2O$ | 0.04 | 32 | 100 |
| Example A-30 | Glucose capric acid monoester | $Mg_6Al_2(OH)_{16}CO_3 \cdot zH_2O$ | 0.04 | 30 | 100 |
| Example A-31 | Glucose pentadecylic acid monoester | $Mg_4Al_2(OH)_{12}Cl_2 \cdot zH_2O$ | 0.04 | 25 | 100 |
| Example A-32 | Glucose pentadecylic acid monoester | $Mg_6Al_2(OH)_{16}CO_3 \cdot zH_2O$ | 0.04 | 30 | 100 |
| Example A-33 | Glucose palmitic acid monoester | $Mg_4Al_2(OH)_{12}Cl_2 \cdot zH_2O$ | 0.04 | 28 | 100 |
| Example A-34 | Glucose palmitic acid monoester | $Mg_6Al_2(OH)_{16}CO_3 \cdot zH_2O$ | 0.04 | 32 | 100 |
| Example A-35 | Glucose dodecanedioic acid monoester | $Mg_6Al_2(OH)_{16}CO_3 \cdot zH_2O$ | 0.04 | 26 | 100 |
| Example A-36 | Fructose lauric acid monoester | $Mg_4Al_2(OH)_{12}Cl_2 \cdot zH_2O$ | 0.04 | 23 | 100 |
| Example A-37 | Fructose lauric acid monoester | $Mg_6Al_2(OH)_{16}CO_3 \cdot zH_2O$ | 0.04 | 30 | 100 |
| Example A-38 | Galactose lauric acid monoester | $Mg_4Al_2(OH)_{12}Cl_2 \cdot zH_2O$ | 0.04 | 24 | 100 |
| Example A-39 | Galactose lauric acid monoester | $Mg_6Al_2(OH)_{16}CO_3 \cdot zH_2O$ | 0.04 | 32 | 100 | at 90° C., and the reaction was made for 4 hours under a reduced pressure of 50 mmHg by stirring with a stirrer.

The obtained reaction solution was cooled, and diluted 5 times with ethylene glycol dimethyl ether to deposit the unreacted myo-inositol. Then, the solid product (potassium carbonate, anhydrous, myo-inositol) was filtered under reduced pressure, and the solvent was distilled away with an evaporator to obtain a condensed dried solid product. Next, the target product was deposited with n-heptane. Then, the unreacted fatty acid was filtered out by filtering under reduced pressure, and the obtained product was further dried under reduced pressure to obtain the target product, inositol capric acid monoester, as a solid. GPC analysis was performed on the obtained inositol capric acid monoester. The purity of inositol capric acid monoester was 89% in molar ratio.

Production Example B-2

Preparation of Inositol Lauric Acid Monoester

Inositol lauric acid monoester was prepared by the same method as that in Production Example B-1 except that 33 mmol of methyl laurate was used instead of methyl caprate. GPC analysis was performed on the obtained inositol lauric acid monoester. The purity of inositol lauric acid monoester was 83% in molar ratio.

Production Example B-3

Preparation of Inositol Palmitic Acid Monoester

Inositol palmitic acid monoester was prepared by the same method as that in Production Example B-1 except that 33 mmol of methyl palmitate was used instead of methyl caprate. GPC analysis was performed on the obtained inositol palmitic acid monoester. The purity of inositol palmitic acid monoester was 72% in molar ratio.

Example B-1

The disproportionation reaction was performed using inositol capric acid monoester prepared in Production Example B-1 as the raw material and commercially available $Mg_4Al_2(OH)_{12}Cl_2 \cdot zH_2O$ as the catalyst. Specifically, 0.4 g of inositol capric acid monoester, 0.04 g of the catalyst, and 1 mL of 1,2-dimethoxyethane as the reaction solvent were charged into a 2 mL screw cap tube bottle, and the reaction was made at the reaction temperature of 60° C. for 24 hours using a thermostat shaking incubator.

After the reaction was completed, the reaction solution was diluted approximately 5 times with 1,2-dimethoxyethane, the catalyst and inositol were removed by filtering with a 0.2 μm filter made of PTFE to obtain an inositol capric acid ester mixture. GPC analysis was performed on part of the obtained mixture. The inositol capric acid monoester conversion rate was 22%, and the inositol capric acid diester selectivity was 100%. The monoester conversion rate can be determined by the following formula (a), and the diester selectivity can be determined by the following formula (b):

monoester conversion rate (%)=(raw material monoester (mol)−unreacted monoester (mol))/raw material monoester (mol)     (a)

diester selectivity (%)=generated diester (mol)/total amount of generated diester, triester, and tetraester (mol)     (b)

Example B-2

An inositol capric acid ester mixture was obtained by the same method as that in Example B-1 except that commercially available $Mg_4Al_2(OH)_{12}CO_3 \cdot zH_2O$ was used as the catalyst. GPC analysis was performed on part of the obtained mixture. The inositol capric acid monoester conversion rate was 25%, and the inositol capric acid diester selectivity was 100%.

Example B-3

An inositol capric acid ester mixture was obtained by the same method as that in Example B-1 except that commercially available $Mg_6Al_2(OH)_{16}CO_3 \cdot zH_2O$ was used as the catalyst. GPC analysis was performed on part of the obtained mixture. The inositol capric acid monoester conversion rate was 20%, and the inositol capric acid diester selectivity was 100%.

Example B-4

The disproportionation reaction was performed using inositol lauric acid monoester prepared in Production Example B-2 as the raw material and commercially available $Mg_4Al_2(OH)_{12}Cl_2 \cdot zH_2O$ as the catalyst. Specifically, 0.4 g of inositol lauric acid monoester, 0.04 g of the catalyst, and 1 mL of 1,2-dimethoxyethane as the reaction solvent were charged into a 2 mL screw cap tube bottle, and the reaction was made at the reaction temperature of 60° C. for 24 hours using a thermostat shaking incubator.

After the reaction was completed, the reaction solution was diluted approximately 5 times with 1,2-dimethoxyethane, and the catalyst and inositol were removed by filtering with a 0.2 μm filter made of PTFE to obtain an inositol lauric acid ester mixture. GPC analysis was performed on part of the obtained mixture. The inositol lauric acid monoester conversion rate was 34%, and the inositol lauric acid diester selectivity was 100%.

Example B-5

An inositol lauric acid ester mixture was obtained by the same method as that in Example B-4 except that commercially available $Mg_4Al_2(OH)_{12}CO_3 \cdot zH_2O$ was used as the catalyst. GPC analysis was performed on part of the obtained mixture. The inositol lauric acid monoester conversion rate was 31%, and the inositol lauric acid diester selectivity was 100%.

Example B-6

An inositol lauric acid ester mixture was obtained by the same method as that in Example B-4 except that commercially available $Mg_6Al_2(OH)_{16}CO_3 \cdot zH_2O$ was used as the catalyst. GPC analysis was performed on part of the obtained mixture. The inositol lauric acid monoester conversion rate was 34%, and the inositol lauric acid diester selectivity was 100%.

Example B-7

An inositol lauric acid ester mixture was obtained by the same method as that in Example B-4 except that commercially available $Mg_{10}Al_2(OH)_{24}Cl_2 \cdot zH_2O$ was used as the catalyst. GPC analysis was performed on part of the obtained mixture. The inositol lauric acid monoester conversion rate was 28%, and the inositol lauric acid diester selectivity was 100%.

Example B-8

An inositol lauric acid ester mixture was obtained by the same method as that in Example B-4 except that commercially available $Mg_{10}Al_2(OH)_{24}CO_3.zH_2O$ was used as the catalyst. GPC analysis was performed on part of the obtained mixture. The inositol lauric acid monoester conversion rate was 26%, and the inositol lauric acid diester selectivity was 100%.

Example B-9

An inositol lauric acid ester mixture was obtained by the same method as that in Example B-4 except that commercially available $Ca_3Al_2(OH)_{10}Cl_2.zH_2O$ was used as the catalyst. GPC analysis was performed on part of the obtained mixture. The inositol lauric acid monoester conversion rate was 28%, and the inositol lauric acid diester selectivity was 100%.

Example B-10

An inositol lauric acid ester mixture was obtained by the same method as that in Example B-4 except that commercially available $Ca_4Al_2(OH)_{10}Cl_2.zH_2O$ was used as the catalyst. GPC analysis was performed on part of the obtained mixture. The inositol lauric acid monoester conversion rate was 29%, and the inositol lauric acid diester selectivity was 100%.

Example B-11

An inositol lauric acid ester mixture was obtained by the same method as that in Example B-4 except that commercially available $Ca_4Mg_6Al_5(OH)_{10}Cl_2.zH_2O$ was used as the catalyst. GPC analysis was performed on part of the obtained mixture. The inositol lauric acid monoester conversion rate was 34%, and the inositol lauric acid diester selectivity was 100%.

Example B-12

The disproportionation reaction was performed using inositol palmitic acid monoester prepared in Production Example B-3 as the raw material and commercially available $Mg_4Al_2(OH)_{12}Cl_2.zH_2O$ as the catalyst. Specifically, 0.4 g of inositol palmitic acid monoester, 0.04 g of the catalyst, and 1 mL of 1,2-dimethoxyethane as the reaction solvent were charged into a 2 mL screw cap tube bottle, and the reaction was made at the reaction temperature of 60° C. for 24 hours using a thermostat shaking incubator.

After the reaction was completed, the reaction solution was diluted approximately 5 times with 1,2-dimethoxyethane, and the catalyst and inositol were removed by filtering with a 0.2 μm filter made of PTFE to obtain an inositol palmitic acid ester mixture. GPC analysis was performed on part of the obtained mixture. The inositol palmitic acid monoester conversion rate was 24%, and the inositol palmitic acid diester selectivity was 100%.

Example B-13

An inositol palmitic acid ester mixture was obtained by the same method as that in Example B-12 except that commercially available $Mg_4Al_2(OH)_{12}CO_3.zH_2O$ was used as the catalyst. GPC analysis was performed on part of the obtained mixture. The inositol palmitic acid monoester conversion rate was 26%, and the inositol palmitic acid diester selectivity was 100%.

Example B-14

An inositol palmitic acid ester mixture was obtained by the same method as that in Example B-12 except that commercially available $Mg_6Al_2(OH)_{16}CO_3.zH_2O$ was used as the catalyst. GPC analysis was performed on part of the obtained mixture. The inositol palmitic acid monoester conversion rate was 23%, and the inositol palmitic acid diester selectivity was 100%.

Comparative Example B-1

The catalyst in Example B-4 was replaced by an inorganic oxide having no hydrotalcite structure $Mg_6Al_2O_9$, and the reaction was performed, but the disproportionation reaction did not progress at all.

The reaction conditions in Examples B-1 to B-14 and Comparative Example B-1 and the results of analysis of the obtained mixtures are shown in Table 6.

TABLE 6

| | Raw material | Catalyst Kind | Amount to be added (g) | Monoester conversion rate (%) | Diester selectivity (%) |
|---|---|---|---|---|---|
| Example B-1 | Inositol capric acid monoester | $Mg_4Al_2(OH)_{12}Cl_2 \cdot zH_2O$ | 0.04 | 22 | 100 |
| Example B-2 | Inositol capric acid monoester | $Mg_4Al_2(OH)_{12}CO_3 \cdot zH_2O$ | 0.04 | 25 | 100 |
| Example B-3 | Inositol capric acid monoester | $Mg_6Al_2(OH)_{16}CO_3 \cdot zH_2O$ | 0.04 | 20 | 100 |
| Example B-4 | Inositol lauric acid monoester | $Mg_4Al_2(OH)_{12}Cl_2 \cdot zH_2O$ | 0.04 | 34 | 100 |
| Example B-5 | Inositol lauric acid monoester | $Mg_4Al_2(OH)_{12}CO_3 \cdot zH_2O$ | 0.04 | 31 | 100 |
| Example B-6 | Inositol lauric acid monoester | $Mg_6Al_2(OH)_{16}CO_3 \cdot zH_2O$ | 0.04 | 34 | 100 |
| Example B-7 | Inositol lauric acid monoester | $Mg_{10}Al_2(OH)_{24}Cl_2 \cdot zH_2O$ | 0.04 | 28 | 100 |
| Example B-8 | Inositol lauric acid monoester | $Mg_{10}Al_2(OH)_{24}CO_3 \cdot zH_2O$ | 0.04 | 26 | 100 |
| Example B-9 | Inositol lauric acid monoester | $Ca_3Al_2(OH)_{10}Cl_2 \cdot zH_2O$ | 0.04 | 28 | 100 |
| Example B-10 | Inositol lauric acid monoester | $Ca_4Al_2(OH)_{10}Cl_2 \cdot zH_2O$ | 0.04 | 29 | 100 |
| Example B-11 | Inositol lauric acid monoester | $Ca_4Mg_6Al_5(OH)_{10}Cl_2 \cdot zH_2O$ | 0.04 | 34 | 100 |
| Example B-12 | Inositol palmitic acid monoester | $Mg_4Al_2(OH)_{12}Cl_2 \cdot zH_2O$ | 0.04 | 24 | 100 |
| Example B-13 | Inositol palmitic acid monoester | $Mg_4Al_2(OH)_{12}CO_3 \cdot zH_2O$ | 0.04 | 26 | 100 |
| Example B-14 | Inositol palmitic acid monoester | $Mg_6Al_2(OH)_{16}CO_3 \cdot zH_2O$ | 0.04 | 23 | 100 |
| Comparative Example B-1 | Inositol lauric acid monoester | $Mg_6Al_2O_2$ | 0.04 | 0 | — |

INDUSTRIAL APPLICABILITY

According to the production method according to the present invention, a diester of polyhydric alcohol and fatty acid can be obtained efficiently.

The invention claimed is:

1. A method of producing a diester of polyhydric alcohol and fatty acid, comprising a step of
reacting a monoester of polyhydric alcohol and fatty acid in the presence of a catalyst containing a hydrotalcite compound to obtain a diester of polyhydric alcohol and fatty acid,
wherein the polyhydric alcohol constituting the monoester of polyhydric alcohol and fatty acid is a sugar or a sugar alcohol.

2. The method according to claim 1, wherein the hydrotalcite compound is a compound represented by the following formula (1):

$$(M^{2+})_{1-x}(M^{3+})_x(OH^-)_{2+x-y}(A^{n-})_{y/n} \quad (1)$$

wherein $M^{2+}$ represents a divalent metal ion, $M^{3+}$ represents a trivalent metal ion, $A^{n-}$ represents an n-valent anion, x represents a positive number of 0.1 to 0.5, y represents a positive number of 0.1 to 0.5, and n represents an integer of 1 or 2.

3. The method according to claim 1, wherein the fatty acid constituting the monoester of polyhydric alcohol and fatty acid has 4 to 24 carbon atoms.

4. The method according to claim 1, wherein the polyhydric alcohol constituting the monoester of polyhydric alcohol and fatty acid is a monosaccharide.

5. The method according to claim 4, wherein the monosaccharide comprises glucose, fructose, or galactose.

6. The method according to claim 1, wherein the polyhydric alcohol constituting the monoester of polyhydric alcohol and fatty acid is inositol.

7. The method according to claim 6, wherein the inositol is myo-inositol.

8. The method according to claim 1, wherein the step is performed in a reaction solution containing at least one solvent selected from the group consisting of an ether compound, a ketone compound, a nitrile compound, a halogenated alkyl compound, a tertiary alcohol compound, an amide compound, an amine compound, a sulfoxide compound, and a linear hydrocarbon compound having 5 to 8 carbon atoms.

9. The method according to claim 1, wherein a reaction temperature in the step is from 50 to 100° C.

10. A method of producing a diester of polyhydric alcohol and fatty acid, comprising a step of
reacting a monoester of polyhydric alcohol and fatty acid in the presence of a catalyst containing a hydrotalcite compound to obtain a diester of polyhydric alcohol and fatty acid,
wherein a reaction temperature in the step is from 50 to 100° C.

11. The method according to claim 10, wherein the polyhydric alcohol constituting the monoester of polyhydric alcohol and fatty acid is a sugar or a sugar alcohol.

12. The method according to claim 10, wherein the hydrotalcite compound is a compound represented by the following formula (1):

$$(M^{2+})_{1-x}(M^{3+})_x(OH^-)_{2+x-y}(A^{n-})_{y/n} \quad (1)$$

wherein $M^{2+}$ represents a divalent metal ion, $M^{3+}$ represents a trivalent metal ion, $A^{n-}$ represents an n-valent anion, x represents a positive number of 0.1 to 0.5, y represents a positive number of 0.1 to 0.5, and n represents an integer of 1 or 2.

13. The method according to claim 10, wherein the fatty acid constituting the monoester of polyhydric alcohol and fatty acid has 4 to 24 carbon atoms.

14. The method according to claim 10, wherein the polyhydric alcohol constituting the monoester of polyhydric alcohol and fatty acid is a monosaccharide.

15. The method according to claim 14, wherein the monosaccharide comprises glucose, fructose, or galactose.

16. The method according to claim 10, wherein the polyhydric alcohol constituting the monoester of polyhydric alcohol and fatty acid is inositol.

17. The method according to claim 16, wherein the inositol is myo-inositol.

18. The method according to claim 10, wherein the step is performed in a reaction solution containing at least one solvent selected from the group consisting of an ether compound, a ketone compound, a nitrile compound, a halogenated alkyl compound, a tertiary alcohol compound, an amide compound, an amine compound, a sulfoxide compound, and a linear hydrocarbon compound having 5 to 8 carbon atoms.

* * * * *